(12) United States Patent
Groninger

(10) Patent No.: US 10,495,454 B2
(45) Date of Patent: *Dec. 3, 2019

(54) INSPECTION PATH DISPLAY

(71) Applicant: General Electric Company, Schenectady, NY (US)

(72) Inventor: Daniel Scott Groninger, Port Royal, PA (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/002,779

(22) Filed: Jun. 7, 2018

(65) Prior Publication Data

US 2018/0292205 A1 Oct. 11, 2018

Related U.S. Application Data

(63) Continuation of application No. 14/865,533, filed on Sep. 25, 2015, now Pat. No. 10,018,465.

(51) Int. Cl.

| G01B 21/00 | (2006.01) |
|---|---|
| G01N 29/22 | (2006.01) |
| G01N 27/90 | (2006.01) |
| G01N 29/06 | (2006.01) |
| G01N 29/265 | (2006.01) |

(52) U.S. Cl.
CPC ............ *G01B 21/00* (2013.01); *G01N 27/90* (2013.01); *G01N 27/9006* (2013.01); *G01N 29/0609* (2013.01); *G01N 29/0645* (2013.01); *G01N 29/22* (2013.01); *G01N 29/265* (2013.01)

(58) Field of Classification Search
CPC .. G01B 21/00; G01N 29/265; G01N 29/0645; G01N 29/0609; G01N 27/90
See application file for complete search history.

(56) References Cited

U.S. PATENT DOCUMENTS

| 4,908,774 A | * | 3/1990 | Lund ................. G01N 29/0645 |
|---|---|---|---|
| | | | 702/39 |
| 6,775,625 B2 | | 8/2004 | Burkhardt et al. |
| 6,914,427 B2 | | 7/2005 | Gifford et al. |

(Continued)

FOREIGN PATENT DOCUMENTS

| EP | 2828775 A1 | 1/2015 |
|---|---|---|
| WO | 8707026 A1 | 11/1987 |
| WO | 9941600 A1 | 8/1999 |

OTHER PUBLICATIONS

GE Sensing & Inspection Technologies; on or before Oct. 31, 2009; General Electric Company; 19 pages.

(Continued)

*Primary Examiner* — Changhyun Yi
(74) *Attorney, Agent, or Firm* — Mintz Levin Cohn Ferris Glovsky and Popeo, P.C.

(57) ABSTRACT

An inspection system, in an embodiment, can be operable with a probe and a position tracker to inspect an object. The system can be operable to display at least one probe travel axis, receive first and second inspection values from the probe, associate the first inspection value with a first position point, and associate the second inspection value with a second position point. The system displays an inspection path based on the associations. The inspection path extends relative to the probe travel axis.

20 Claims, 15 Drawing Sheets

(56) References Cited

U.S. PATENT DOCUMENTS

| | | |
|---|---|---|
| 8,036,836 B2 | 10/2011 | Liu et al. |
| 8,301,400 B2 | 10/2012 | Beard et al. |
| 8,306,779 B2 | 11/2012 | Beard et al. |
| 10,018,465 B2 * | 7/2018 | Groninger ............... G01B 21/00 |
| 2006/0048578 A1 | 3/2006 | Dickinson et al. |
| 2010/0220910 A1 | 9/2010 | Kaucic |
| 2010/0235037 A1 * | 9/2010 | Vian ....................... G07C 5/008 |
| | | 701/31.4 |
| 2012/0297881 A1 | 11/2012 | Steinhoff et al. |
| 2012/0303333 A1 | 11/2012 | Stuke |
| 2014/0178853 A1 | 6/2014 | Groninger et al. |
| 2014/0185912 A1 * | 7/2014 | Lim ........................ G06T 7/001 |
| | | 382/141 |
| 2015/0039245 A1 | 2/2015 | Langlois et al. |
| 2016/0341671 A1 | 11/2016 | Maass |

OTHER PUBLICATIONS

NDT Resource Center, Data Presentation, 3 pages, Retrieved from the Internet: https://www.nde-ed.org/EducationResources/CommunityCollege/Ultr- asonic/EquipmentTr.com.

Reconfigurable FPGAs for data compression in ultrasonic non-destructive testing by David J. Darlington, et al., IEE: DSP Chips in Real Time Measurement and Control, Sep. 25, 1997, 4 pages.

The NDT Technician, Focus Benefits and Limitations of Ultrasonic Testing Multiplexers by L. Byron Makarwich, Jan. 2005, 16 pages.

Humans elimination human error, GE Measurement & Control, Jul. 2014, 8 pages.

Display-Complex Impedance Plane (eddy scope), 3 pages, Retrieved from the Internet: https://www.ndeed.org/EducationResources/CommunityCollege/EddyC- urrents/Instrument.com.

Kim W S Ed—Institute of Electrical and Electronics Engineers, Graphical Operator Interface for Space Telerobotics, Proceedings of the International Conference on Robotics and Automation Atlanta, Los Alamitos, IEEE Comp. Soc. Press, US, May 2-6, 1993, pp. 761-768, vol. Conf. 10, XP010095364, ISBN: 978-0-8186-3450-5, DOI: 10.1109/ROBOT.1993.292237.

V Moshkovich, Recent Advances in the Ultrasonic Inspection Recording and Reporting Instrumentation: Part 2. Straight Beam Inspection and Imaging, NDT.net, Nov. 1, 2003, vol. No. 8, Issue No. 11, XP055315251, Retrieved from the Internet:URL:http://www.ndt.net/article/v08nl1/passi2/passi2.htm [retrieved on Oct. 31, 2016].

International Search Report and Written Opinion issued in connection with corresponding Application No. PCT/US2016/044141 dated Nov. 10, 2016.

* cited by examiner

INSPECTION PATH DISPLAY

CROSS REFERENCE TO RELATED APPLICATIONS

This application is a continuation of, and claims priority to, U.S. patent application Ser. No. 14/865,533, filed Sep. 25, 2016, and entitled METHOD AND DEVICE FOR MEASURING FEATURES ON OR NEAR AN OBJECT, the entirety of which is incorporated herein by reference.

BACKGROUND

Non-destructive testing (NDT) can be used to inspect parts for flaws. Testers can use NDT tools to determine, for example, whether aircraft panels have developed flaws or whether manufactured parts conform to predetermined specifications.

Known NDT tools, such as ultrasound sensors and eddy current sensors, typically rely upon the conventional gating process. In the conventional gating process, the tester uses a sensor to gather data from a conforming part serving as a model. If the sensor produces data having a peak and a valley, for example, the tester records a peak alarm gate above the peak and a valley alarm gate below the valley. Then the tester proceeds to test a part for potential flaws. If the tested part's peak falls within the peak alarm gate, the part has a flaw. If the tested part's valley falls within the valley alarm gate, the part has another flaw.

This conventional gating process can be challenging, complex and error-prone. It requires a significant amount of training and experience to learn how to create and analyze conventional gates. Furthermore, the conventional gating process can be troublesome when testing relatively intricate parts with different regions having different or complex geometries. For example, it can be difficult to create and analyze conventional gates for the relatively small transition regions of a part. This difficulty can cause the tester to inadvertently fail to create gates. The omission of gates can cause the tester to miss important flaws in the tested part. Overlooked flaws can lead to safety risks and quality problems. The known ultrasound, eddy current and other types of NDT tools suffer from the same or similar disadvantages. It is therefore advantageous to overcome, or lessen the effects of, the problems, disadvantages and shortcomings described above.

SUMMARY

The subject matter disclosed herein relates to the inspection of objects.

The inspection system, in an embodiment, can be operable in conjunction with a probe and a position tracker to inspect an object. The system can be operable to display at least one probe travel axis, receive first and second inspection values from the probe, associate the first inspection value with a first position point, and associate the second inspection value with a second position point. The system displays an inspection path based on the associations. The inspection path extends relative to the probe travel axis, facilitating the inspection and evaluation process.

Advantages that may be realized in the practice of some disclosed embodiments of the inspection system include: (a) the enhanced visualization of flaws or non-conformities in relatively small, short, complex or intricate regions of inspectable objects; (b) the decrease or elimination of the failure to inspect relatively small, short, complex or intricate regions of inspectable objects; (c) the increased amount of information that can be gathered in the inspection of objects with small, short, complex or intricate regions; (d) the enhanced detection of significant deviations of inspectable objects compared to reference objects; (e) the facilitation of the understanding and interpretation of probe-based inspection results; and (f) the improved graphical representation of inspection result data through the display of spatially-intuitive inspection paths. Though the system provides such advantages with respect to objects with small, short, complex or intricate regions, it should be appreciated that the system also provides such advantages for the inspection of larger and simpler objects, such as flat panels with substantially uniform surfaces.

In an embodiment, the inspection system includes a data storage device storing a plurality of instructions. The data storage is accessible by at least one processor, and the at least one processor is operable with a probe and a position tracker to inspect an object. The processor is operable according to the instructions to operate with a display device to: (a) display at least one probe travel axis, wherein the at least one probe travel axis extends through a plurality of inspection position points; (b) receive a first inspection value derived from the probe when the probe is positioned at a first object point corresponding to a first one of the inspection position points, wherein the first inspection value relates to a characteristic of the object at the first object point; (c) receive a second inspection value derived from the probe when the probe is positioned at a second object point corresponding to a second one of the inspection position points, wherein the second inspection value relates to the characteristic of the object at the second object point; and (d) perform an association. The step of performing the association includes associating the first inspection value with the first inspection position point and associating the second inspection value with the second inspection position point. Furthermore, the processor is operable according to the instructions to operate with the display device to display an inspection path based on the association, wherein the inspection path extends relative to the at least one probe travel axis. In an embodiment, the inspection path facilitates inspection by graphically indicating object information related to the characteristic of the object and by graphically indicating probe information related to positions of the probe relative to the object.

In another embodiment, the inspection system includes at least one processor operable with a probe and a position tracker to inspect an object. The at least one processor is programmed to operate with a display device to: (a) display at least one probe travel axis, wherein the at least one probe travel axis extends through a plurality of inspection position points; (b) receive a first inspection value derived from the probe corresponding to the probe being positioned at a first object point corresponding to a first one of the inspection position points, wherein the first inspection value relates to a characteristic of the object at the first object point; (c) receive a second inspection value from the probe corresponding to the probe being positioned at a second object point corresponding to a second one of the inspection position points, wherein the second inspection value relates to the characteristic of the object at the second object point; and (d) perform an association. The step of performing the association includes associating the first inspection value with the first position point and associating the second inspection value with the second position point. Also, the processor is programmed to operate with the display device to: (i) display an inspection path based on the association, wherein the inspection path extends relative to the at least one probe travel axis; and (ii) display a reference path extending relative to the at least one probe travel axis. The reference path is based on a first reference value corresponding to the characteristic at the first object point, and the reference path is also based on a second reference value corresponding to the characteristic at the second object point.

In an embodiment, the inspection method includes: (a) graphically displaying at least one probe travel axis, wherein the at least one probe travel axis extends through a plurality of inspection position points; (b) receiving a first inspection value derived from the probe corresponding to the probe being positioned at a first object point corresponding to a first one of the inspection position points, wherein the first inspection value relates to a characteristic of the object at the first object point; (c) receiving a second inspection value derived from the probe corresponding to the probe being positioned at a second object point corresponding to a second one of the inspection position points, wherein the second inspection value relates to the characteristic of the object at the second object point; (d) performing an association comprising: (i) associating the first inspection value with the first position point; and (ii) associating the second inspection value with the second position point; and (iii) displaying an inspection path based on the association, wherein the inspection path extends relative to the at least one probe travel axis. In an embodiment, the inspection path facilitates inspection by graphically indicating object information related to the characteristic of the object and by graphically indicating probe information related to a variable position of the probe relative to the object.

The above embodiments are exemplary only. Other embodiments are within the scope of the disclosed subject matter.

BRIEF DESCRIPTION OF THE DRAWINGS

So that the manner in which the features of the disclosed subject matter can be understood, a detailed description of the disclosed subject matter may be had by reference to certain embodiments, some of which are illustrated in the accompanying drawings. It is to be noted, however, that the drawings illustrate only certain embodiments of this disclosed subject matter and are therefore not to be considered limiting of its scope, for the scope of the disclosed subject matter encompasses other embodiments as well. The drawings are not necessarily to scale, emphasis generally being placed upon illustrating the features of certain embodiments of the disclosed subject matter. In the drawings, like numerals are used to indicate like parts throughout the various views.

DETAILED DESCRIPTION

Embodiments of the disclosed subject matter provide an inspection system that can be operable in conjunction with a probe and a position tracker to inspect an object. The system, in an embodiment, can display at least one probe travel axis, receive first and second inspection values from the probe, associate the first inspection value with a first position point, and associate the second inspection value with a second position point. The system can display an inspection path based on the associations. The inspection path can extend relative to the probe travel axis. In an embodiment, the system can also display an overlay of the inspection path relative to a reference path. To the extent the two paths are not identical, such paths form a track or ladder with a plurality of rungs. The rungs represent deviations from the reference path. Rungs that exceed a maximum deviation setting can indicate a failure outcome for the inspected object. Other embodiments are within the scope of the disclosed subject matter.

Figure 1:
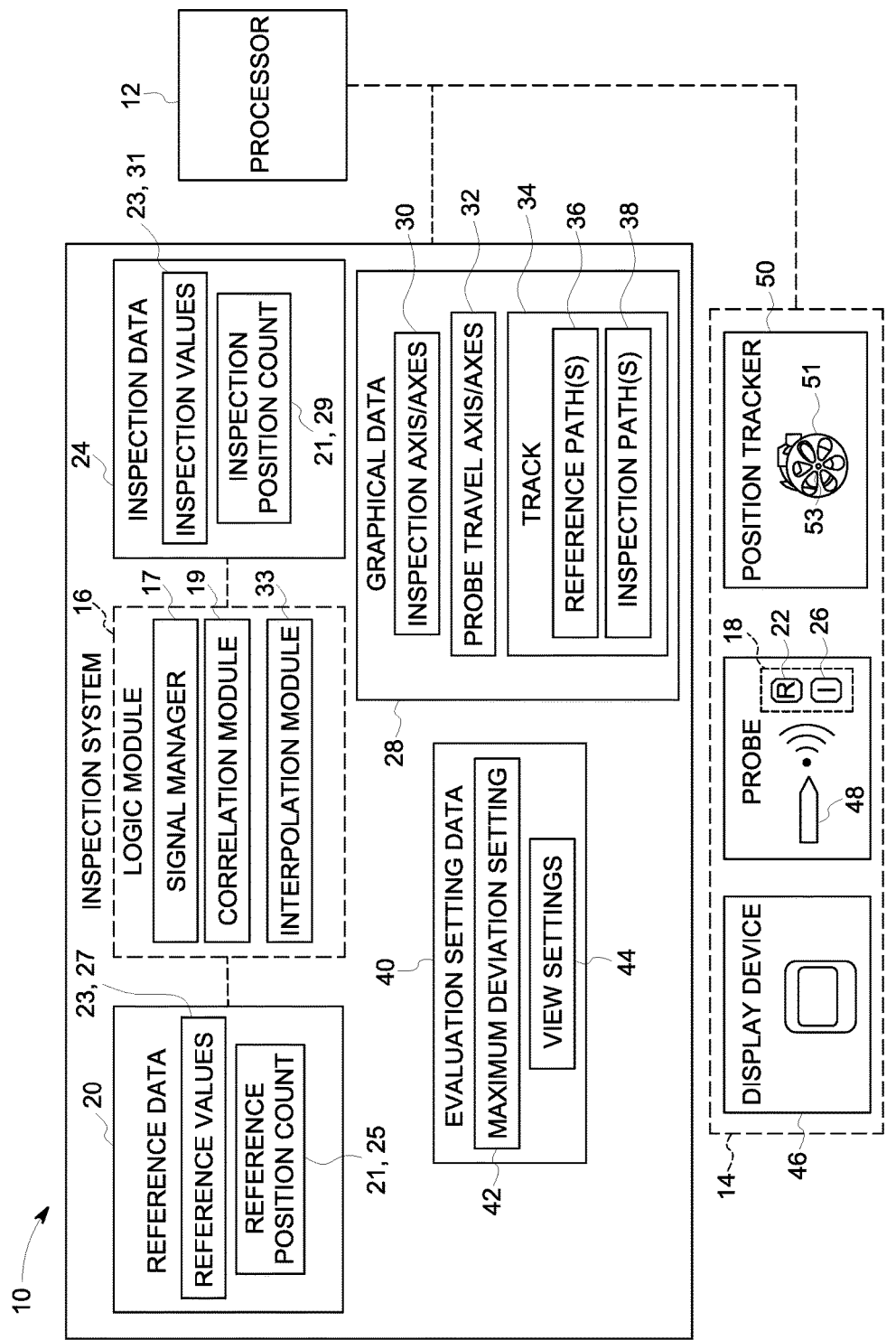
FIG. 1 is block diagram illustrating an embodiment of the inspection system used in conjunction with at least one processor and a plurality of input/output devices.

In an embodiment illustrated in FIG. 1, the testing or inspection system 10 can be operatively coupled to at least one processor 12. As described further below, the processor 12 can include a control circuit, controller, microprocessor or other form of circuitry configured to process data or otherwise execute machine-readable instructions. The processor 12 can be operatively coupled to a plurality of input/output (I/O) devices 14. In operation, the user operates the I/O devices 14 for inspection purposes, and the processor 12 uses the system 10 to generate failure outcome alerts and pass outcome alerts for the user.

With continued reference to FIG. 1, the system 10, in an embodiment, can include: (a) computer code, machine-readable instructions or logic module 16; (b) data derived from or related to an object 18, such as: (i) reference data 20 derived from and related to a reference object 22; and (ii) inspection data 24 derived from and related to an inspectable object 26; (d) graphical data 28 usable by the processor 12 to generate one or more graphical inspection axes 30 and one or more graphical probe travel axes 32, and a graphical ladder or track 34 formed by a combination of a reference path 36 and an inspection path 38 as described further below; and (e) evaluation setting data 40 usable by the processor 12 to receive a user-adjustable, maximum deviation setting 42 from the user and to receive variable view settings 44 from the user. The I/O devices 14, in an embodiment, can include a display device 46, a sensor or probe 48, and a position monitor or position tracker 50.

In an embodiment, the logic module 16 can include computer code, including, but not limited to, field programmable gate arrays (FPGAs) in the form of software code, one or more computer programs, or machine-readable instructions executable by the processor 12. In another embodiment, the logic module 16 can include one or more application-specific integrated circuits (ASICs), FPGAs in the form of circuits, or other hardware circuit components configured to control the logic and operation of the system 10. In an embodiment, the logic module 16 can include a signal manager 17, a correlation module 19 and an interpolation module 33. The signal manager 17 can control the processing, conditioning, amplifying, filtering and analysis of the incoming signals received from the probe 48 and position tracker 50. As described further below, the correlation module 19, in an embodiment, can synchronically associate the position points of probe travel axis 32 with values 23 derived from the probe 48.

As described further below, the system 10 is operable in a reference mode and an inspection mode. In the reference mode, object 18 is the reference object 22 having an exemplary or benchmark characteristic. In the inspection mode, the object 18 is an inspectable object 26 to be tested for pass or failure in comparison to the benchmark or reference characteristic of the reference object 22. The processor 12 uses the system 10 to generate and maintain a position count 21 based on the changing position of the probe 48 relative to the object 18. The processor 12 also generates or processes values 23 based on signals received from the probe 48. In the reference mode, the signals are reference signals, the position count 21 is a reference position count 25, and values 23 are reference values 27. In the inspection mode, the signals are inspection signals, the position count 21 is an inspection position count 29, and values 23 are inspection values 31. Accordingly, reference data 20 includes reference values 27 and reference position count 25. Likewise, inspection data 24 includes inspection values 31 and inspection position count 29. As described below, the processor 12 processes the reference data 20 and inspection data 24 to generate graphical output indicating a pass or failure for an inspectable object 26.

In an embodiment, the reference data 20 can include a library of reference data sets, where each reference data set corresponds to a unique reference object 22. In such embodiment, the logic module 16 can direct the processor 12 to generate an average reference data set based on the average of the multiple reference data sets. The processor 12 can then use the average reference data set to generate the track 34 as described below.

In another embodiment, the system 10 can include a historical data library. The historical data library can store the historical data sets of each reference object 22 previously inspected and each inspectable object 26 previously inspected. Each such data set can include the raw positional data or count 21 and the raw signal value data or values 23. In an embodiment, the system 10 can include a report generator operable to generate output, including graphs, charts, tables and other reports describing such historical data sets. Such output can facilitate the evaluation and interpretation of the inspection results of the system 10.

The probe 48, in an embodiment, can include one or more transducers operable for non-destructive testing of objects 18. The probe 48 can have different shapes and sizes, including, but not limited to, the pencil-shaped probes illustrated in FIGS. 3-4. Depending upon the embodiment, the probe 48 can be an eddy current probe, an acoustic, sonic or ultrasound probe, an optical probe, such as a camera, an infrared or thermal probe, a high penetration radiation probe, such as an X-ray machine, a gas sensing probe or gas sensor, or any other suitable type of probe operable to measure, gather or generate object-related information related to, or derived from, one or more types of characteristics of an object 18.

Depending upon the type of probe 48, the probe 48 can measure or detect different classes or types of characteristics of the objects 18, including, without limitation, physical characteristics (e.g., shape and size), electrical characteristics, and chemical characteristics. The detectable characteristics of objects 18 can include, but are not limited to, color, cavities, voids, crack initiation and propagation, cracks, through-cracks, crack depth, thickness, geometry, shape, size, film thickness, reflectivity, strain distribution and magnitude, surface finish, surface flaws, alloy content, anisotropy, cold work, local strain, hardness, composition, contamination, corrosion, crystal structure, electrical conductivities, thermal conductivities, flakes, heat treatment, hot tears, inclusions, ion concentrations, laps, lattice strain, layer thickness, moisture content, polarization, seams, segregation, shrinkage, state of cure, tensile strength, disbonds, damping factor, degree of cure, degree of impregnation, degree of sintering, delaminations, density, elastic moduli, grain size, inclusions, mechanical degradation, misalignment, porosity, radiation degradation, structure of composites, surface stress, tensile, shear, compressive strength, wear, anisotropy, bonding, composition, emissivity, heat contours, plating thickness, porosity, reflectivity, stress and other characteristic types.

For each characteristic type, the probe 48 can sense a magnitude or dimension of, or related to, the object 18. For a physical characteristic, for example, the probe 48 can sense a dimension such as a 2 mm depth of a valley surface below the surface of an object 18. For an electrical characteristic, for example, the probe 48 can sense a dimension such as the magnitude or level of the conductivity of an object 18. For a chemical characteristic, for example, the probe 48 can sense a dimension such as the concentration or percentage of Ethanol in an object 18.

As illustrated in FIGS. 1-4, the position tracker 50, in an embodiment, can be a position encoder or an electromechanical device configured to monitor and record the varying positions of the probe 48 relative to object 18. In an embodiment, the position tracker 50 can be a rotary position encoder having: (a) a disk or wheel 51; (b) a shaft 53 coupled to the wheel 51; (c) position circuitry including a position processor operatively coupled to the shaft 53; (d) a position tracker cable 55 connected to the position circuitry; and (e) a probe coupler or mount 57 configured to attach or mount the position tracker 50 to the probe 48.

Figure 2:
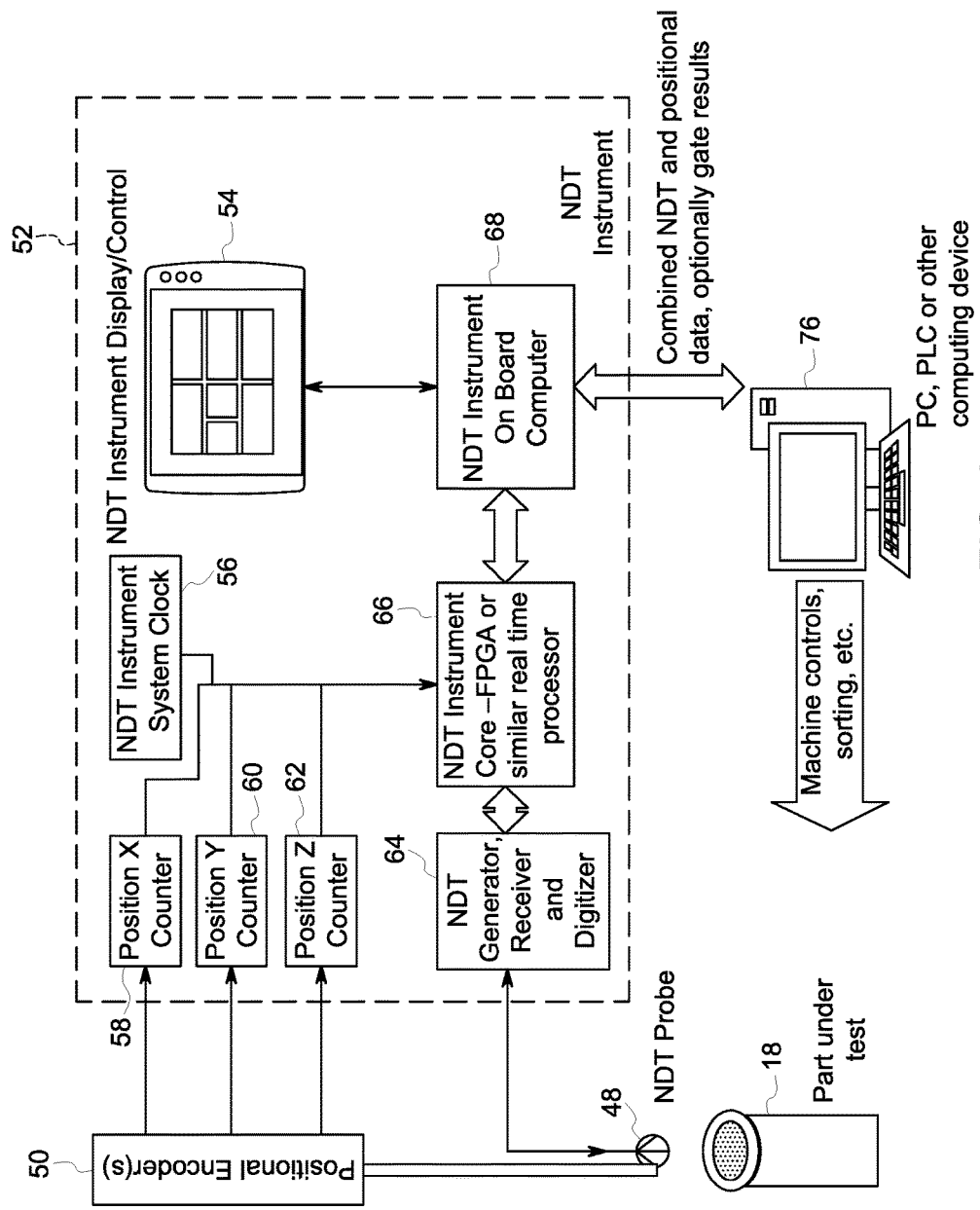
FIG. 2 is a block diagram illustrating an embodiment of the NDT instrument used in conjunction with at least one computing device, a position tracker and a probe for inspecting objects.

In an embodiment illustrated in FIG. 2, the logic module 16 is incorporated into an NDT instrument 52, and the NDT instrument 52 incorporates an NDT display device 54. The NDT instrument 52 can be operatively coupled to the probe 48 and the probe position tracker 50. Using the probe 48, the user can inspect an object 18. In an embodiment, the NDT instrument 52 can include: (a) a clock 56 operable to provide a common time system for the position X counter 58, position Y counter 60 and position Z counter 62; (b) an NDT generator, receiver and digitizer 64 operable to cause the probe 48 to generate signals, to receive signals from the probe 48 based on interaction with the object 18, and to digitize the received signals for digital processing; (c) a core FPGA or real time processor 66 operable to manage and manipulate the signals generated by and received from the probe 48; and (d) an onboard computer 68 operatively coupled to the processor 66.

In an embodiment, the position X counter 58 is operable to count incremental movement of the probe 48 relative to the object 18 along a spatial X-axis, such as probe travel axis Px 70 described below with respect to FIGS. 6-7. Position Y counter 60 is operable to count incremental movement of the probe 48 relative to the object 18 along a spatial Y-axis, such as probe travel axis Py 72 described below with respect to FIGS. 6-7. Position Z counter 62 is operable to count incremental movement of the probe 48 relative to the object 18 along a spatial Z-axis, such as probe travel axis Pz 74 described below with respect to FIGS. 6-7.

In an embodiment, the onboard computer 68 can include a central processing unit or data processor and one or more memory devices or data storage devices operatively coupled to the data processor. In the example illustrated, the NDT instrument 52 can be in communication with a computing device 76, including, but not limited to, a personal computer, programmable logic controller (PLC) or server. In such embodiment, the computing device 76 stores or otherwise processes the reference data 20, inspection data 24, graphical data 28 and evaluation setting data 40. By operating the computing device 76, the user can generate displays of tracks 34 for object testing purposes.

Depending upon the embodiment, the NDT instrument 52 can be coupled to the computing device 76 through a data cable or wireless communication channel. In an embodiment, the NDT instrument 52 can include or otherwise incorporate all of the components, logic, data and elements of system 10 shown in FIG. 1. In another embodiment, all of the components, logic and elements of the NDT instrument 52 can be incorporated into the computing device 76.

Figure 3:
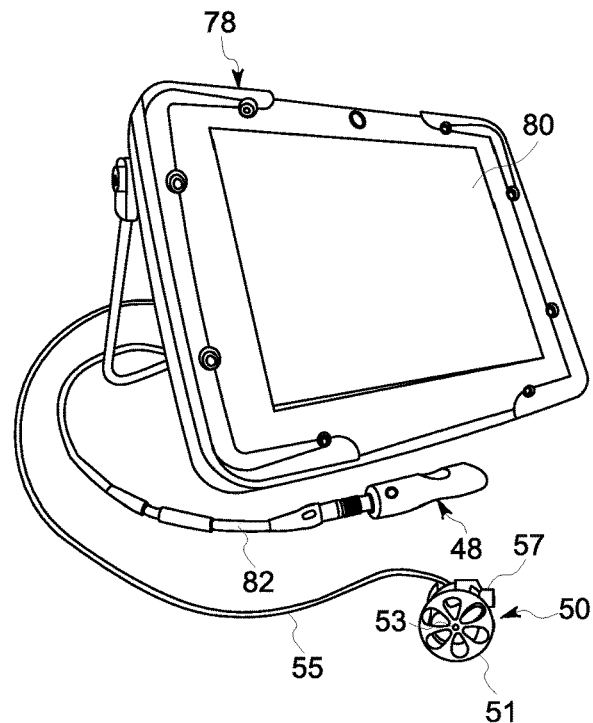
FIG. 3 is a front isometric view of an embodiment of an NDT inspection unit operatively coupled to a probe and a position tracker.

In an embodiment illustrated in FIG. 3, part or all of the system 10 can be incorporated into a portable NDT unit 78. NDT unit 78 can include: (a) an NDT processor housed within the NDT unit 78; (b) a display device 80, such as a monitor, screen, LCD panel or other suitable visual output device; (c) a probe 48 operatively coupled to the NDT processor through a probe cable 82; and (d) a position tracker 50 operatively coupled to the NDT processor through a position tracker cable 55.

Figure 4:
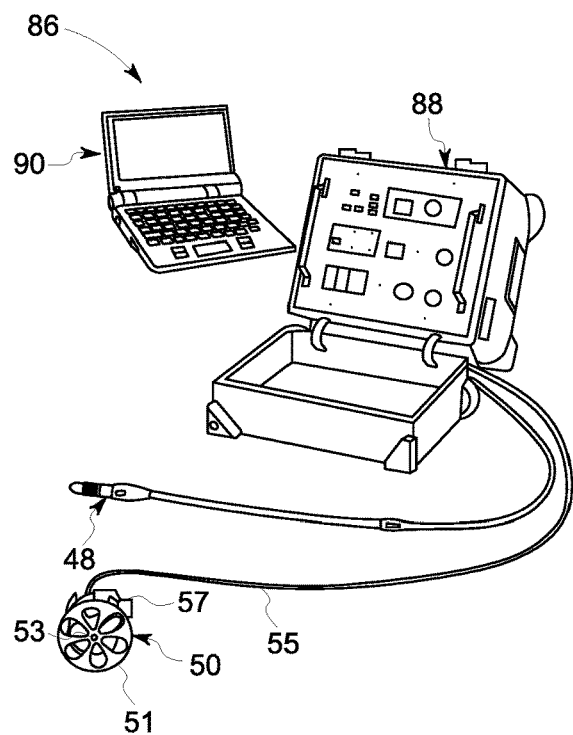
FIG. 4 is a front isometric view of an embodiment of an NDT inspection assembly including a laptop computer, a probe and a position tracker.

In an embodiment illustrated in FIG. 4, part or all of the system 10 can be incorporated into a portable NDT assembly 86. NDT assembly 86 includes an NDT unit 88 operatively coupled to a mobile computing device, such as laptop computer 90. The NDT assembly 86 can include: (a) an NDT processor housed within NDT unit 88; (b) a probe 48 operatively coupled to the NDT processor through a probe cable 82; and (c) a position tracker 50 operatively coupled to the NDT processor through a position tracker cable 55.

Figure 5:
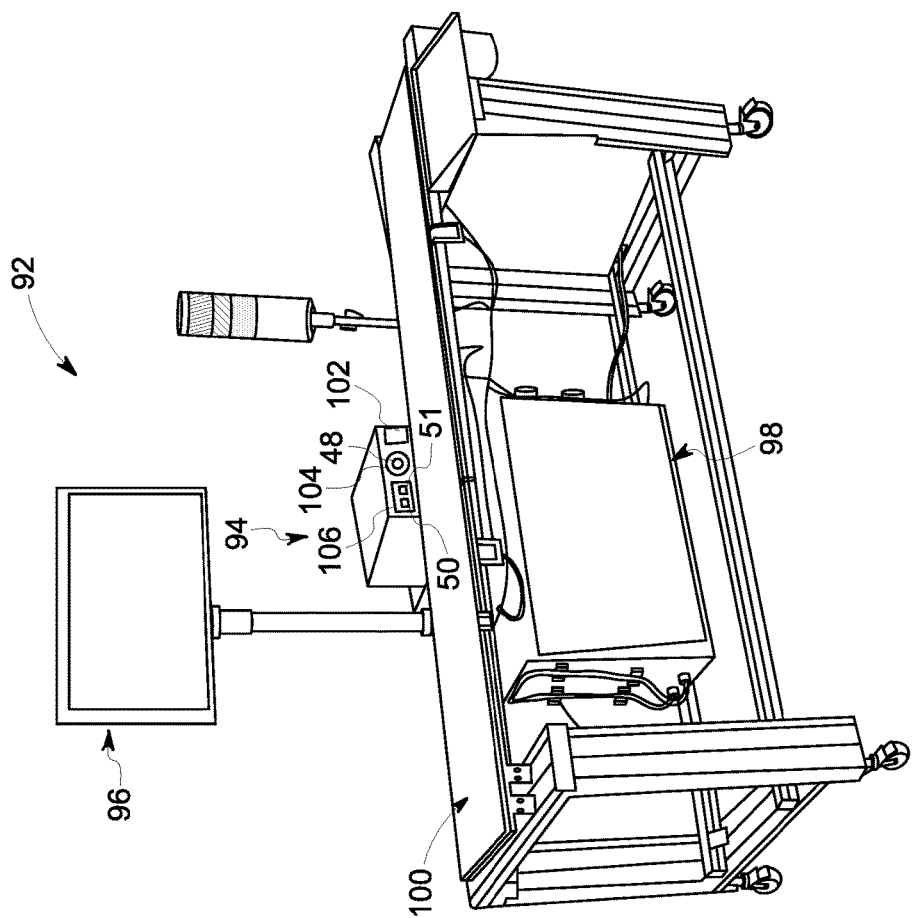
FIG. 5 is a front isometric view of an embodiment of an NDT inspection station having a probe and a position tracker.

Referring to FIG. 5, in an embodiment, part or all of the system 10 can be incorporated into an NDT inspection station 92. The NDT inspection station 92 can include: (a) an NDT inspection unit 94; (b) a mounted display device 96 operatively coupled to the inspection unit 94; (c) a computer 98 operatively coupled to the inspection unit 94; (d) a tabletop or work surface 100 for supporting objects 18 during inspection; (e) a fixture 102 configured to securely hold each object 18 during inspection; (f) a motorized probe driver 104 configured to hold, drive and control the movement of the probe 48 relative to the object 18; and (g) a position tracker holder 106 configured to mount the position tracker 50 to the probe 48 so that the wheel 51 rolls upon the work surface 100 or another surface of the inspection station 92 or the object 18. The NDT inspection station 92 enables objects 18 to be inspected in an automated or semi-automated fashion.

Figure 6:
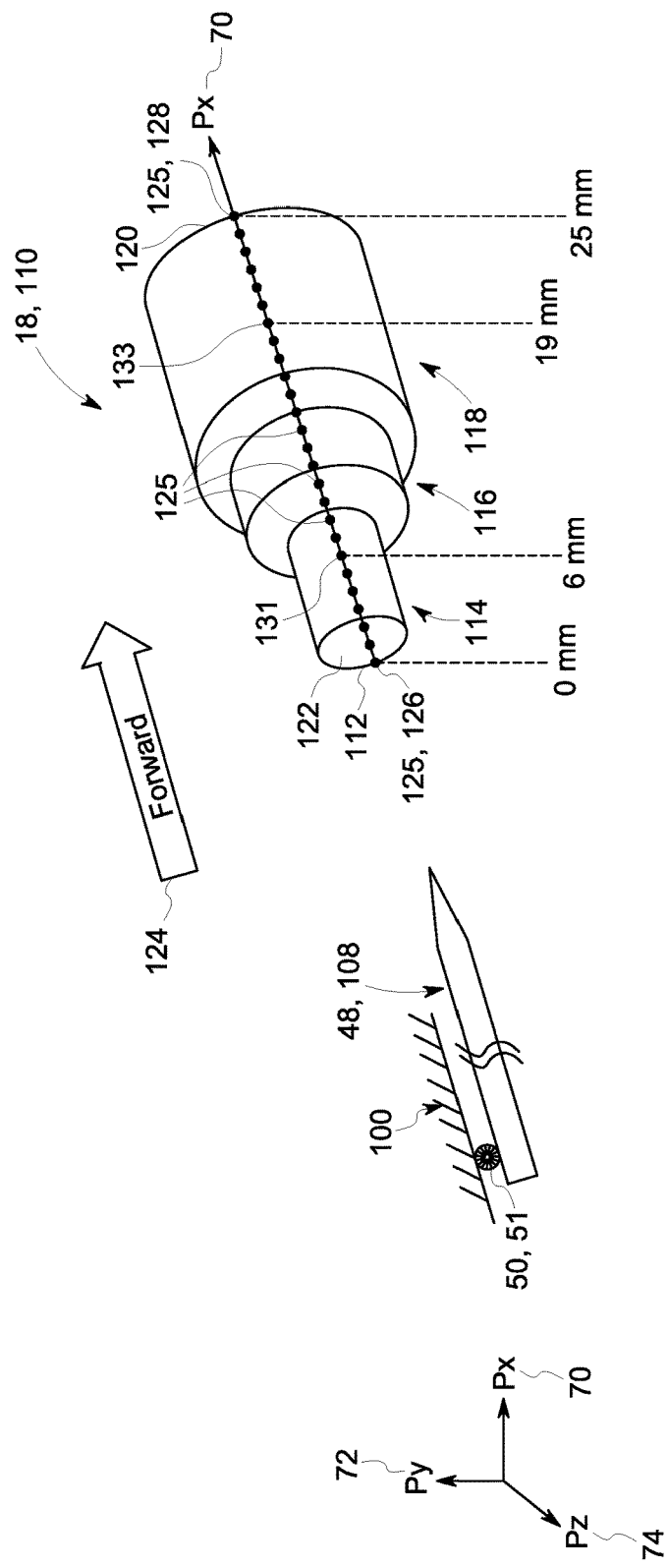
FIG. 6 is an isometric view of an embodiment of an eddy current probe and a multi-diameter, tubular object inspectable by the eddy current probe as such probe moves along a probe travel axis.

Referring to FIG. 6, in an embodiment, probe 48 is an eddy current probe 108 having an electromagnetic component including one more magnetic coils. In one example, the eddy current probe 108 generates outgoing magnetic field signals directed toward a tubular object 110. Based on the characteristic of the tubular object 110 at different locations on the tubular object 110, the tubular object 110 can induce different electrical currents or eddy currents in the electromagnetic component. The eddy currents correspond to impedance values. Each impedance value depends on the resistance and inductive reactance caused by the tubular object 110 which, in turn, depends on the characteristic of the tubular object 110 at a designated location on the tubular object 110. The impedance value (Z) can be calculated as the square root of the sum of: (a) the square of the resistive value (R); and (b) the square of the inductive reactance value (X) according to the following formula: $Z=\sqrt{(R^2+X^2)}$. In addition, the impedance value has an associated phase angle which can be calculated as follows: Tan(phase angle)=X/R. The impedance value and phase angle can be graphically plotted or indicated using an impedance plane diagram. Each impedance value can be object-related data or object-related information that is related to or otherwise derived from a characteristic of the tubular object 110. The eddy current signal on the impedance plane can react in a variety of different ways due to different values received at different locations on the tubular object 110 for assessing the characteristic of the tubular object 110.

For example, if an unexpected crack were present in tubular object 110, fewer eddy currents would form than expected at that location of the crack, the resistance would decrease unexpectedly at that location, and the inductive reactance would increase unexpectedly at that location. The impedance value for the crack would reflect the decreased resistance and increased inductive reactance. In this way, the eddy current probe 108 can enable varying impedance values to be generated which correspond to different dimensions of the physical characteristic of the tubular object 110 at different locations.

In the example illustrated in FIG. 6, tubular object 110 has a left end or starting boundary object point 112, a first region 114 having a first diameter, a second region 116 having a second diameter greater than the first diameter, a third region 118 having a third diameter greater than the second diameter, and a right end or ending boundary object point 120. The eddy current probe 108 can be gradually moved into tubular object 110 for inspection purposes. In this example, the eddy current probe 108 is coupled to the position tracker 50 which, in turn, rolls upon a work surface 100 or an inner surface 122 of tubular object 110.

In operation, the user or an automated probe driver begins moving the eddy current probe 108 from the starting boundary 112, along the inner surface 122, in a forward direction 124 along or relative to probe travel axis Px 70. During the movement of the probe 108, the wheel 51 makes contact with, and rolls on, the work surface 100 or the inner surface 122 of tubular object 110. Based on the rotation of the wheel 51, the processor 12 (FIG. 1) determines the changing position of the eddy current probe 108 relative to the tubular object 110.

In this example, there are twenty-six vertical marks or position points 125 on probe travel axis Px 70. Position points 125 are equally spaced apart by one millimeter. The first mark or starting position point 126 corresponds to zero probe travel or a zero millimeter position point. The twenty-sixth mark or ending position point 128 corresponds to a full probe travel or a twenty-five millimeter position point. For each position point 125 on probe travel axis Px 70, there can be a corresponding object point of the tubular object 110. For example, the starting position point 126 is at the same location as the starting boundary object point 112, and the ending position point 128 is at the same location as the ending boundary object point 120. It should be appreciated, however, that depending upon the orientation of the tubular object 110, the object points can be located below, above, to the right of or to the left of the probe travel axis Px 70. Therefore, as the eddy current probe 108 travels past the position points 125 of axis Px 70, the eddy current probe 108 travels past the object points.

Referring to FIGS. 1 and 6, as the eddy current probe 108 is moved relative to the tubular object 110, the processor 12 uses the system 10 to generate and maintain the position count 21. The processor 12 also generates or processes the values 23 based on signals received from the eddy current probe 108. As described further below, each position count 21 is associated with the particular value 23 derived from the particular signal generated when the eddy current probe 108 was located at such position count 21. Using this count-value data, as described further below, the processor 12 is operable to display a track 34 representing, for example, the geometry of the tubular object 110 along the probe travel axis Px 70 compared to the geometry of a reference object 22 along the probe travel axis Px 70.

When the eddy current probe 108 is moved to position point 131 in region 114, for example, the eddy current probe 108 generates an impedance value of Z1. The correlation module 19 automatically associates position point 131 with impedance value Z1. In an embodiment, the processor 12 executes the correlation module 19 to instantly associate position point 131 with impedance value Z1 at the moment when eddy current probe 108 is located at position point 131. Continuing with this example, the eddy current probe 108 is moved to position point 133 in region 118. When the eddy current probe 108 is located at position point 133, the eddy current probe 108 generates an impedance value of Z2. The correlation module 19 automatically associates position point 133 with impedance value Z2. In an embodiment, the processor 12 executes the correlation module 19 to instantly associate position point 133 with impedance value Z2 at the moment when eddy current probe 108 is located at position point 133. In an embodiment, each value 23 (FIG. 1) is an impedance value, a phase angle value or an eddy current factor. The eddy current factor can be any value based on, or derived at least in part from, the impedance value, the phase angle value or a combination of such values. The following table A illustrates an example of such correlation:

TABLE A

| POSITION POINT | VALUE | | |
|---|---|---|---|
| | Impedance | Phase Angle | Eddy Current Factor |
| 0 mm | Z1 | A1 | E1 |
| 1 mm | Z1 | A1 | E1 |
| 2 mm | Z1 | A1 | E1 |
| 3 mm | Z1 | A1 | E1 |
| 4 mm | Z1 | A1 | E1 |
| 5 mm | Z1 | A1 | E1 |
| 6 mm (131 in FIG. 6) | Z1 | A1 | E1 |
| . | . | . | . |
| . | . | . | . |
| . | . | . | . |
| 19 mm (133 in FIG. 6) | Z2 | A2 | E2 |
| . | . | . | . |
| . | . | . | . |
| . | . | . | . |
| 25 mm (128 in FIG. 6) | Z2 | A2 | E2 |

Figure 7:
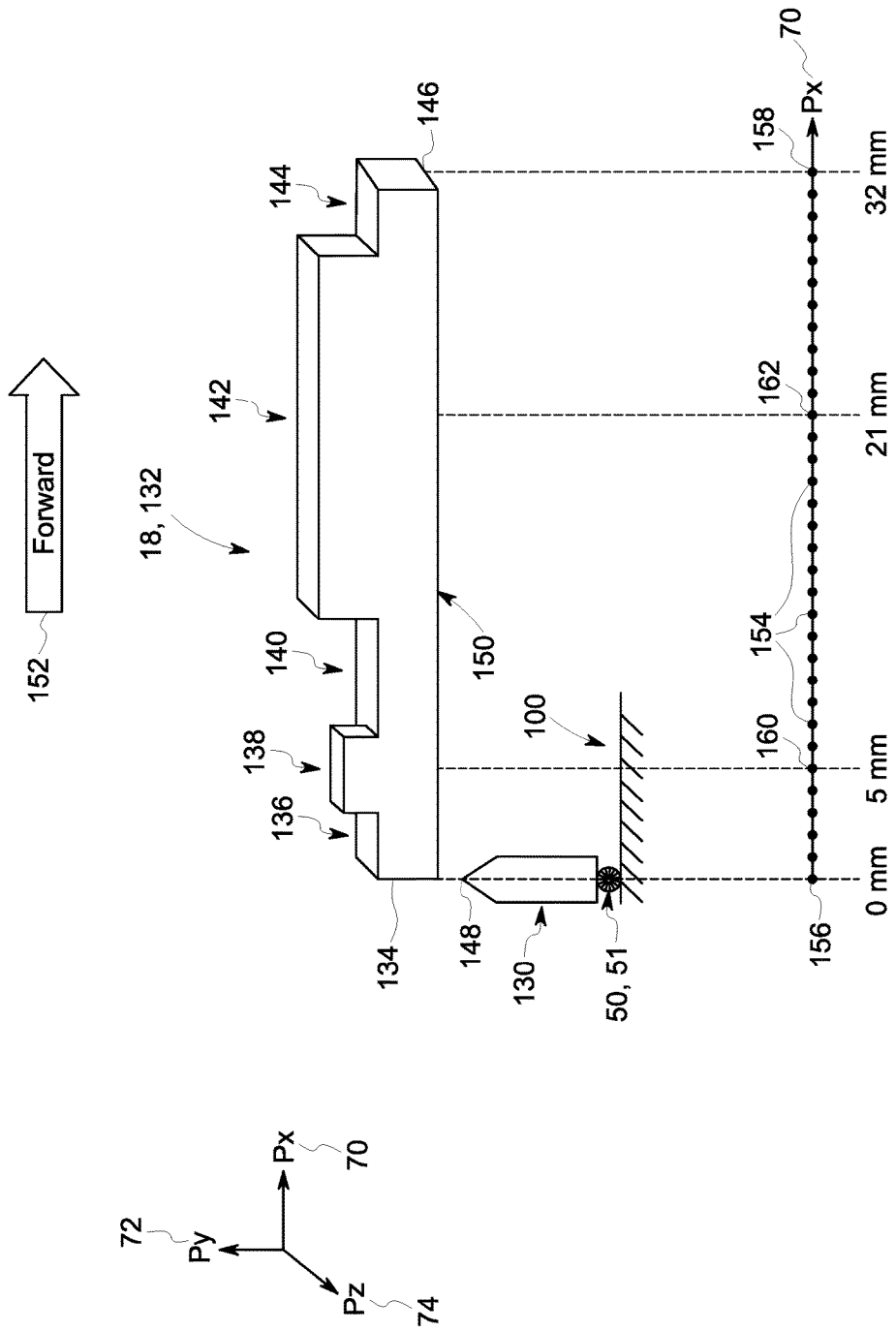
FIG. 7 is an isometric view of an embodiment of an ultra sound probe and a stepped object inspectable by the ultra sound probe as such probe moves along a probe travel axis.

Referring to FIG. 7, in an embodiment, the probe 48 can be an ultrasound probe 130. In operation, the ultrasound probe 130 pulses sonic wave signals, in cycles, at a suitable frequency level, such as between 0.5 MHz and 25 MHz. In the illustrated example, as the ultrasonic wave strikes the step-shaped or stepped object 132 or a reflector portion of the stepped object 132, the stepped object 132 causes a pulse reflection or echo signal. The echo signal has an amplitude value and a time of flight. The time of flight is the time elapsed between the probe's generation of the pulse and the probe's receipt of the corresponding echo signal. The amplitude value and time of flight can be plotted and viewed as an A-scan graph, where time can be plotted on the X-axis, and signal strength (e.g., amplitude value) can be plotted on the Y-axis. The signal strength value and time of flight provide object-related information related to the one or more characteristics of the stepped object 132. For example, if an unexpected internal crack were present in the stepped object 132, the amplitude value would be lower than expected, and the time of flight would be lower than expected. In another example, if a continuous region in the stepped object 132 were thicker than expected, the amplitude value would be lower than expected, and the time of flight would be greater than expected. In this way, the ultrasound probe 130 determines varying sound amplitude values and time of flight values which correspond to the different dimensions of a characteristic of the stepped object 132.

In the example illustrated in FIG. 7, the stepped object 132 has a left end or starting boundary object point 134, a first region 136 having a first thickness, a second region 138 having a second thickness greater than the first diameter, a third region 140 having a third thickness equal to the first thickness, a fourth region 142 having a fourth thickness greater than the third thickness, a fifth region 144 having a fifth thickness equal to the third thickness, and a right end or ending boundary object point 146. The ultrasound probe 130 can be slid gradually along, and in physical contact with, the stepped object 132 for inspection purposes. For example, the user or automated probe driver brings the probe tip or head 148 into physical contact with the surface 150 while sliding the probe head 148 from left to right in the forward direction 152. In this example, the ultrasound probe 130 is coupled to the position tracker 50 which, in turn, rolls upon a work surface 100 or the surface 150 of the stepped object 132.

In operation, the user or an automated probe driver begins moving the ultrasound probe 130 from the starting boundary 134, along the surface 150, in the forward direction 152 along or relative to probe travel axis Px 70. During the movement of the ultrasound probe 130, the wheel 51 makes contact with, and rolls on, the work surface 100 or the surface 150 of stepped object 132. Based on the rotation of the wheel 51, the processor 12 (FIG. 1) determines the changing position of the ultrasound probe 130 relative to the stepped object 132.

In this example, there are thirty-three vertical marks or position points 154 on travel axis Px 70. Position points 154 are equally spaced apart by one millimeter. The first mark or starting position point 156 corresponds to zero probe travel or a zero millimeter position point. The thirty-third mark or ending position point 158 corresponds to a full probe travel or a thirty-two millimeter position point. For each position point 154 on probe travel axis Px 70, there can be a corresponding object point of the stepped object 132. For example, the starting position point 156 is at the same location as the starting boundary object point 134, and the ending position point 158 is at the same location as the ending boundary object point 146. It should be appreciated, however, that depending upon the orientation of the stepped object 132, the object points can be located below, above, to the right of or to the left of the probe travel axis Px 70. Therefore, as the ultrasound probe 130 travels past the position points 154 of probe travel axis Px 70, the ultrasound probe 130 travels past the object points.

Referring to FIGS. 1 and 7, as the ultrasound probe 130 is moved relative to the stepped object 132, the processor 12 uses the system 10 to generate and maintain the position count 21. The processor 12 also generates or processes the values 23 based on signals received from the ultrasound probe 130. As described further below, each position count 21 is associated with the particular value 23 derived from the particular signal generated when the ultrasound probe 130 was located at such position count 21. Using this count-value data, as described further below, the processor 12 is operable to display a track 34 representing, for example, the geometry of the stepped object 132 along the probe travel axis Px 70 compared to the geometry of a reference object 22 along the probe travel axis Px 70.

When the ultrasound probe 130 is moved to position point 160 in region 138, for example, the ultrasound probe 130 generates a signal strength value of S1 and a time of flight value of T1. The correlation module 19 automatically associates position point 160 with signal strength value S1 and time of flight value T1. In an embodiment, the processor 12 executes the correlation module 19 to instantly associate position point 160 with such values at the moment when ultrasound probe 130 is located at position point 160. Continuing with this example, the ultrasound probe 130 is moved to position point 162 in region 142. When the ultrasound probe 130 is located at position point 162, the ultrasound probe 130 generates a signal strength value of S2 and a time of flight value of T2. The correlation module 19 automatically associates position point 162 with signal strength value S2 and time of flight value T2. In an embodiment, the processor 12 executes the correlation module 19 to instantly associate position point 162 with such values at the moment when ultrasound probe 130 is located at position point 162. In an embodiment, each value 23 (FIG. 1) is a signal strength value, a time of flight value or an ultrasound factor. The ultrasound factor can be any value based on, or derived at least in part from, the signal strength value, the time of flight value or a combination of such values. The following table B illustrates an example of such correlation:

TABLE B

| POSITION POINT | VALUE | | |
|---|---|---|---|
| | Signal Strength | Time of Flight | Ultrasound Factor |
| 0 mm | S1 | T1 | U1 |
| 1 mm | S1 | T1 | U1 |
| 2 mm | S1 | T1 | U1 |
| 3 mm | S1 | T1 | U1 |
| 4 mm | S2 | T2 | U2 |
| 5 mm (160 in FIG. 7) | S2 | T2 | U2 |
| • | • | • | • |
| • | • | • | • |
| • | • | • | • |
| 32 mm (158 in FIG. 7) | S1 | T1 | U1 |

In an embodiment, the logic module 16 of the system 10 can include a reset module. Each time a different object is staged for inspection, the reset module can automatically re-correlate or re-synchronize the position count 21 with the applicable values 23 derived from the applicable object. In effect, the reset module would delete or clear the value data from the foregoing tables A and B for each new inspection.

Figure 8:
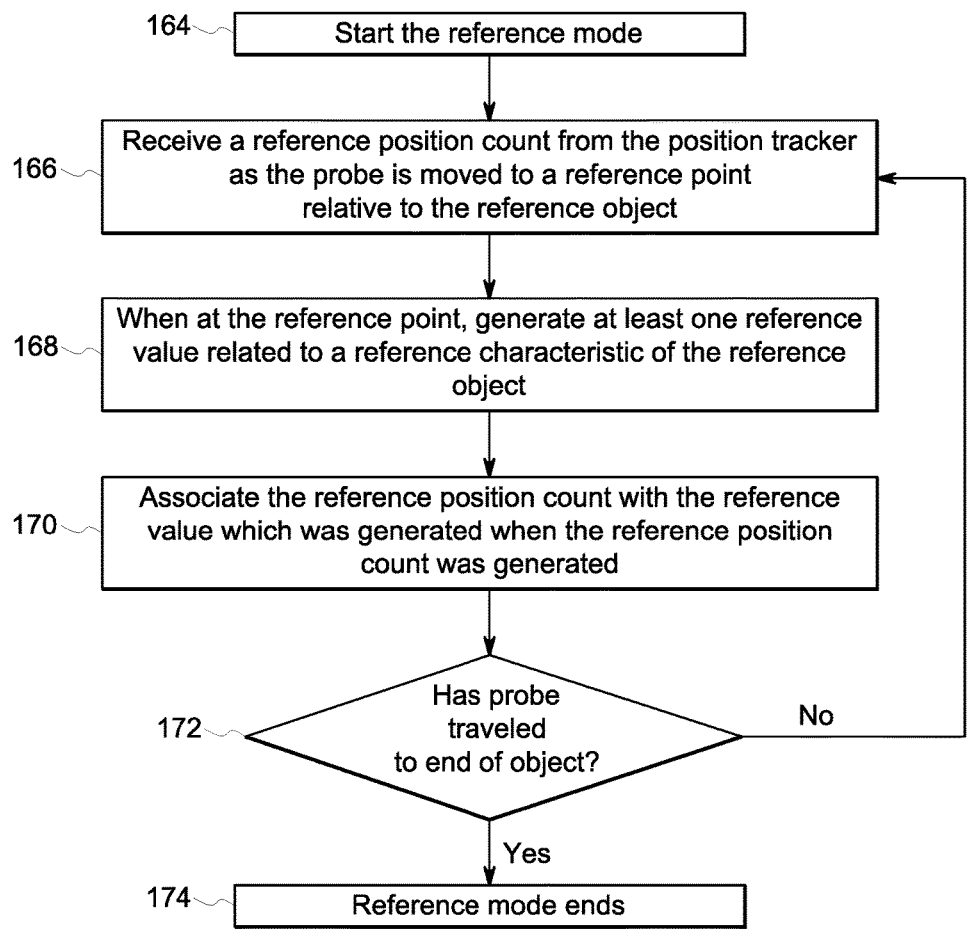
FIG. 8 is a flow chart illustrating an embodiment of the method of operation of the reference mode of the inspection system.
Figure 9:
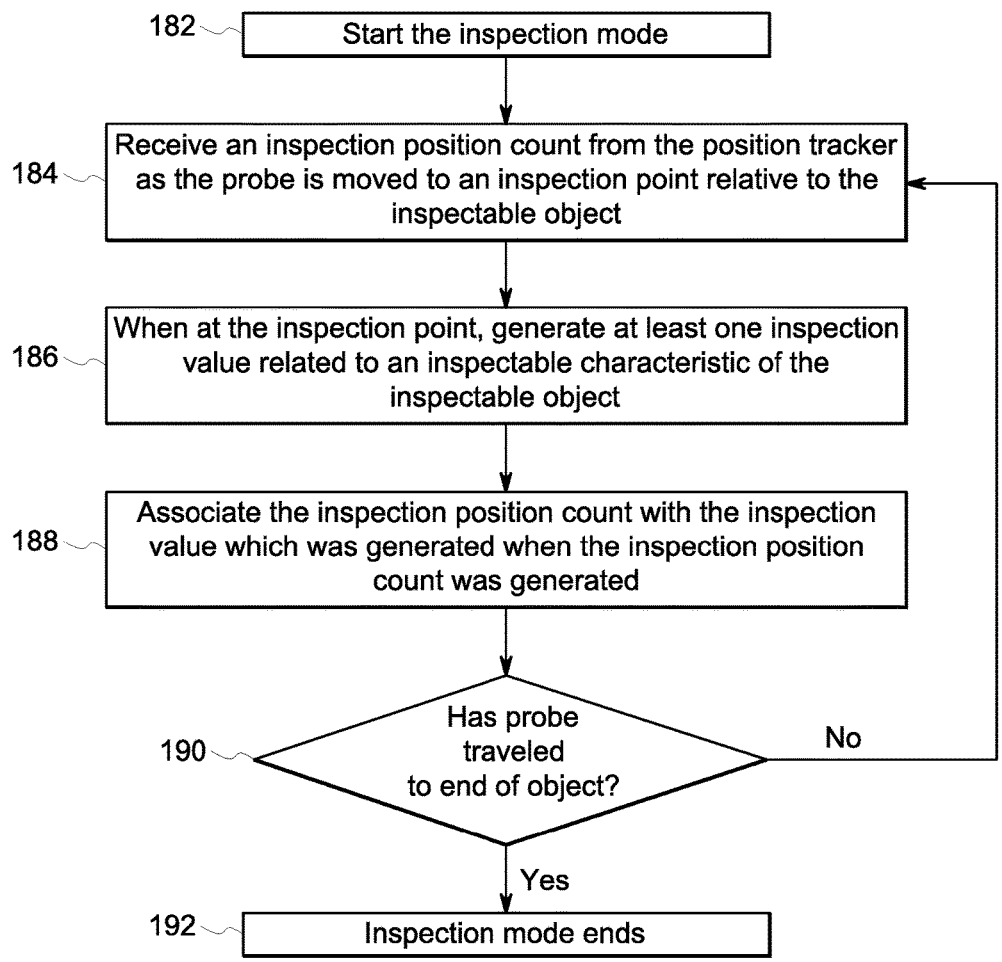
FIG. 9 is a flow chart illustrating an embodiment of the method of operation of the inspection mode of the inspection system.
Figure 10:
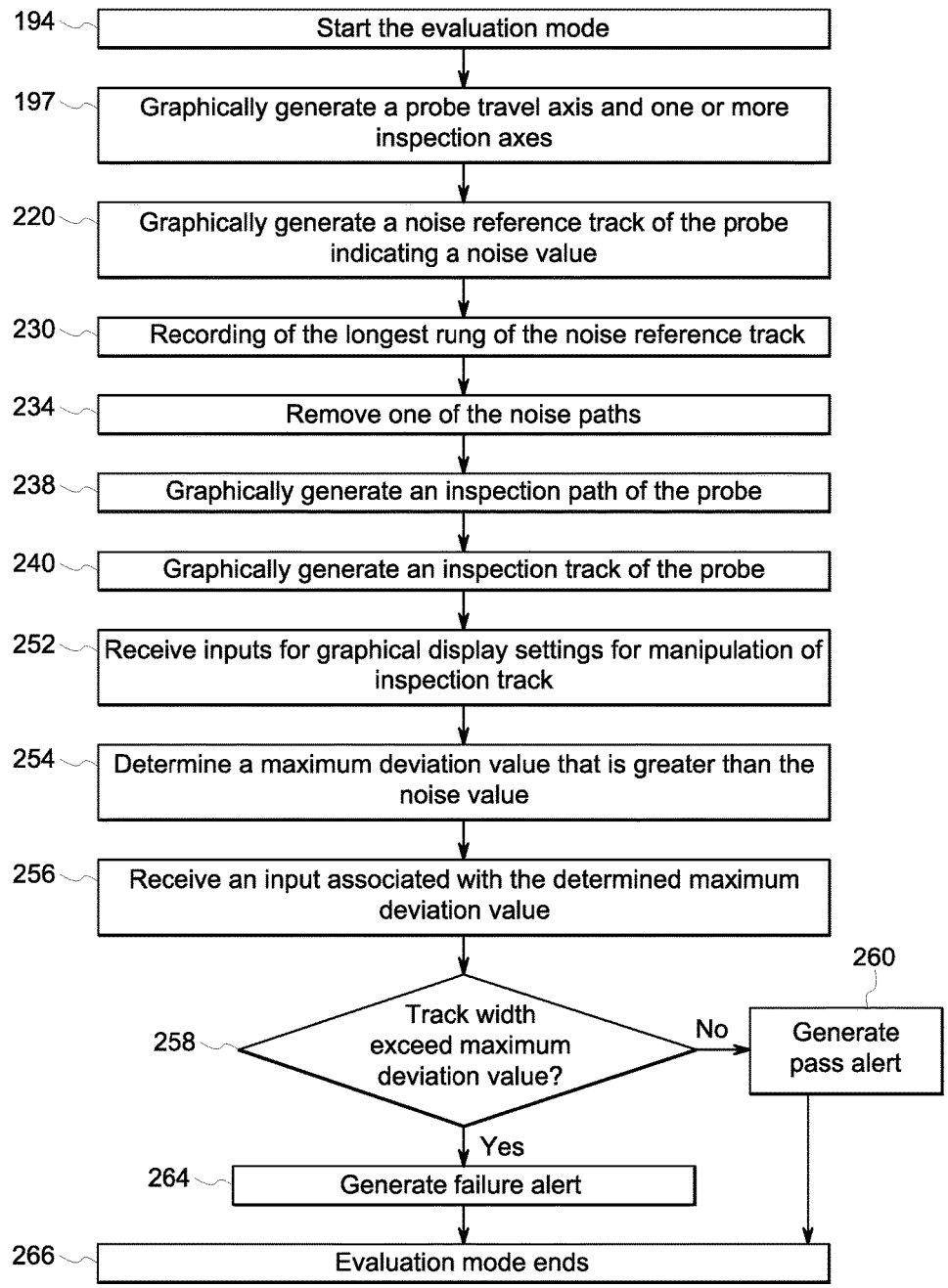
FIG. 10 is a flow chart illustrating an embodiment of the method of operation of the evaluation mode of the inspection system.

In an embodiment, the system 10 can be operable in a reference mode, then an inspection mode and then an evaluation mode. FIGS. 8-10 illustrate the operation of such modes in an example involving the eddy current probe 108 (FIG. 6). Depending upon the embodiment, the same or similar modes and mode steps can occur for the use of the ultrasound probe 130 illustrated in FIG. 7 and for other types of probes. The different modes shown in the figures are exemplary only, and the blocks can be altered, added, removed, or rearranged.

Referring to FIGS. 1, 6 and 8, in the reference mode, the user inspects tubular object 110 (serving as a reference object) to collect benchmark signal data. The tubular object 110 is used for modeling purposes to serve as a benchmark for future comparison purposes. When the reference mode starts, as indicated by block 164, the processor 12 receives a reference position count 25 (FIG. 1) from the position tracker 50 as indicated by block 166. Here, the position tracker 50 generates the reference position count 25 based on the probe's passing of the position points 125 (serving as reference position points) including a start position point 126 (serving as a start reference point), a position point 131 (serving as an intermediate reference point) and a finish position point 128 (serving as a finish reference point) on the probe travel axis Px 70.

Referring to FIG. 6, in this example, the probe travel axis Px 70 is the same as the longitudinal object axis (serving as the reference object axis) extending through the tubular object 110. Depending upon the embodiment, however, the object axis can be the same as the probe travel axis Px 70 or different from, but parallel with, the probe travel axis Px 70. Since in this example, the object axis is the same as probe travel axis Px 70, the object axis has twenty-six position points 125, including position points 131 and 133. The position points 125, including position points 131 and 133, serve as reference position points in the reference mode.

As indicated by block 168 in FIG. 8, when the eddy current probe 108 is at position point 131, the processor 12 generates a reference value 27 (FIG. 1). Based on the operation of the eddy current probe 108, the reference value 27 is an impedance value. Next, referring to FIGS. 1 and 8, the processor 12, directed by the correlation module 19, associates the reference position count 25 with the reference value 27, as indicated by block 170. In the example illustrated in FIG. 6, the processor 12 associates reference position point 131, the six millimeter mark, with a numeric impedance reference value of Z1.

As indicated by decision diamond 172 in FIG. 8, the processor 12 repeats this process until, for each reference position point 125 (FIG. 6) passed by the eddy current probe 108, the system 10 stores the reference value 27 (FIG. 1) corresponding to such reference position point 125. Referring to FIGS. 6 and 8, once the eddy current probe 108 travels to the end 120 of the tubular object 110, the reference mode ends as indicated by block 174.

Referring to FIGS. 1 and 6, in an embodiment of the reference mode, the user or automated probe driver performs a plurality of passes through or across the tubular object 110. This multi-pass approach is performed to gather and assess signal noise data. With two passes, for example, the system 10 generates two sets of reference position counts 25 and associated reference values 27. As described further below with respect to FIG. 14, the system 10 uses these two data sets to graphically generate two reference paths 176 and 178. The reference paths 176 and 178 are displayed to represent a noise reference track 180. As described below, the user can compare the reference paths 176 and 178 to each other to assess the typical, normal or expected level of signal noise present in the inspection process.

After the reference mode, the system 10 can then be operated in the inspection mode. Referring to FIGS. 1 and 6, in the inspection mode, the system 10 operates with the same logic and methodology as described for the reference mode in FIG. 8 except that: (a) the tubular object 110 serves as an inspectable object 26 instead of a reference object 22; (b) the position tracker 50 generates inspection position count 29 instead of the reference position count 25; and (c) the processor 12 generates inspection values 31 instead of reference values 27.

Referring to FIGS. 1, 6 and 9, the inspection mode starts as indicated by block 182. As indicated by block 184, the processor 12 receives the inspection position count 29 (FIG. 1) from the position tracker 50. In the inspection mode, the position points 125 (serving as inspection position points) include a position point 126 (serving as a start position point), a position point 131 (serving as an intermediate position point) and a position point 128 (serving as a finish position point). When the eddy current probe 108 is at position point 126 (FIG. 6), the processor 12 generates the first inspection value 31 related to an inspectable characteristic (e.g., shape or contour) of the tubular object 110, as indicated by block 186. Next, the processor 12 associates the first inspection position count 29 with the first inspection value 31, as indicated by block 188. As indicated by decision diamond 190, the processor 12 repeats these steps 184, 186 and 188 until the eddy current probe 108 has traveled to the end 120 the tubular object 110. This ends the inspection mode as indicated by block 192.

Figure 11:
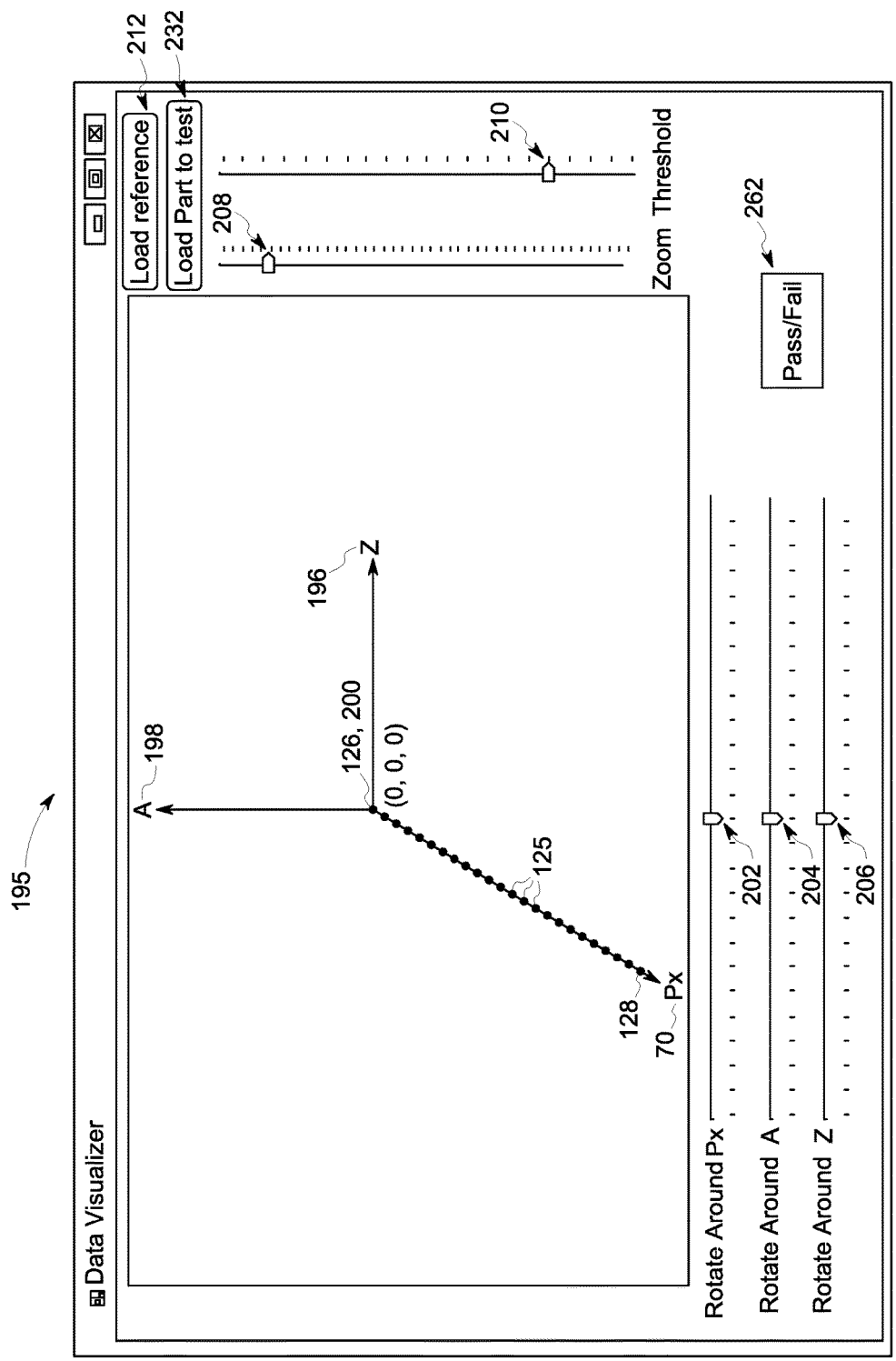
FIG. 11 is a top view of an example of an embodiment of the graphical interface of the inspection system illustrating the probe travel axis and multiple inspection axes.

Referring to FIGS. 1, 6 and 10-15, the evaluation mode starts after the inspection mode as indicated by block 194 in FIG. 10. In response to a user input or start activation, the processor 12 causes the display device 46 to display a graphical evaluation interface 195. In the embodiment illustrated in FIG. 11, graphical evaluation interface 195 displays a probe travel axis Px 70 and a plurality of inspection axes—impedance magnitude axis Z 196 and impedance phase angle axis A 198, as indicated by block 197 (FIG. 10) and as shown in FIG. 11. As shown, the axes 70, 196 and 198 share a common point 200 and represent three dimensions. In this example, the common point 200 has three coordinates (0, 0, 0), including a spatial coordinate of zero for the probe travel axis Px 70, an impedance value coordinate of zero for the impedance magnitude axis Z 196, and an impedance phase angle coordinate of zero for the impedance phase angle axis A 198.

In an embodiment not illustrated, the system 10 can gather spatial information, including position counts 21 (FIG. 1), along three probe travel axes including probe travel axis Px 70, probe travel axis Py 72 and probe travel axis Pz 74 shown in FIG. 6. In such embodiment, the interface 195 can display five axes 70, 72, 74, 196 and 198 representing five dimensions.

Referring to FIG. 11, the interface 195 can include a plurality of different control elements operable by the user to provide inputs and control commands to the processor 12. In the illustrated embodiment, the interface 195 includes rotational view adjusters 202, 204 and 206 associated with axes 70, 198 and 196, respectively. Also, the interface 195 can include zoom adjuster 208 and threshold adjuster 210. As described below, the user can control these adjusters to manipulate the displayed images.

Figure 12:
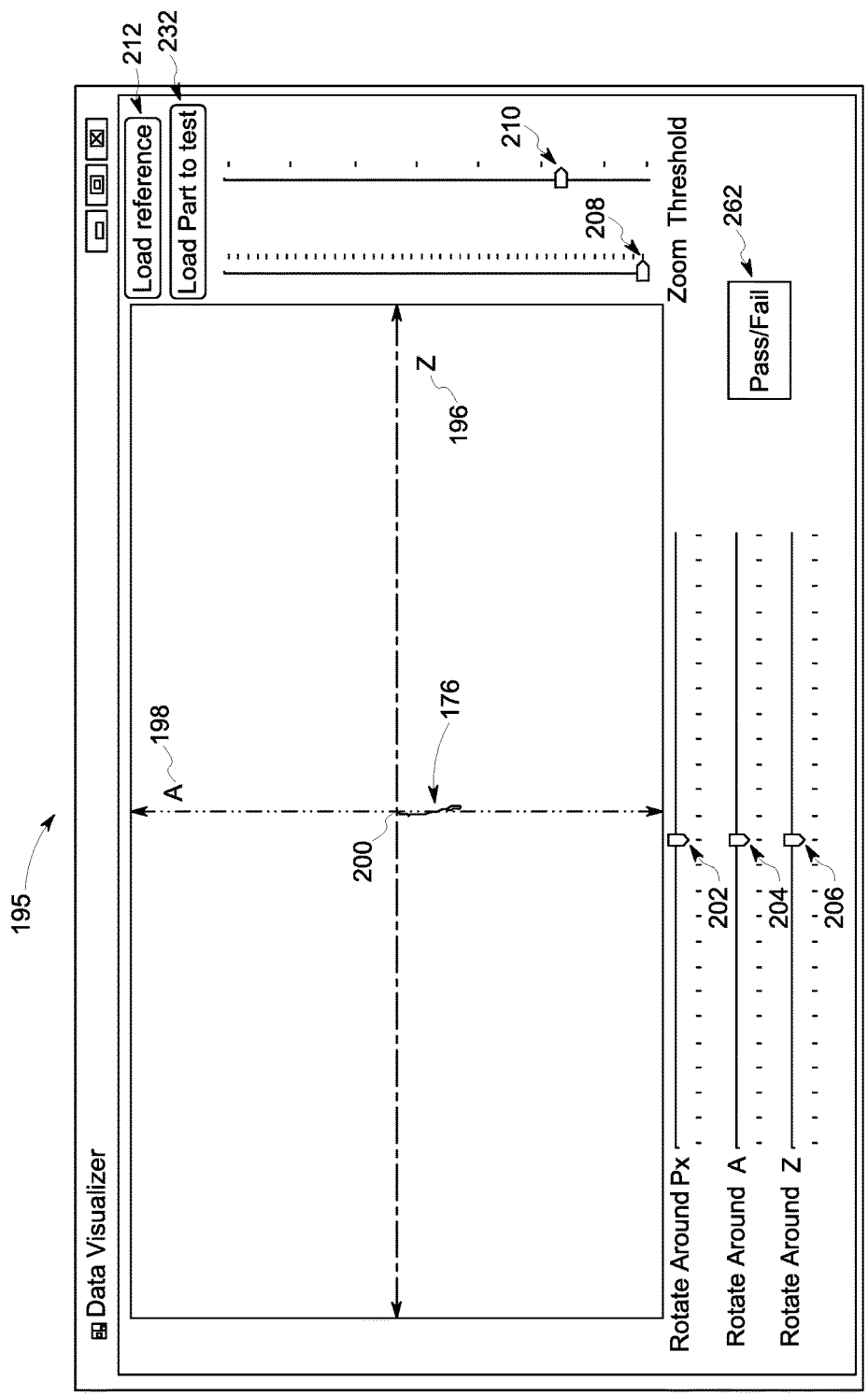
FIG. 12 is a top view of an embodiment of the graphical interface of the inspection system illustrating an example of the reference path before being rotated or enlarged.

In the example illustrated in FIG. 11, the user can press a load reference input element 212. In response, the interface 195 can display the reference path 176 as illustrated in FIG. 12. By controlling or adjusting one or more of the rotational view adjusters 202, 204 and 206, the user can cause the interface 195 to change the angular view of reference path 176. Also, the user can operate the zoom adjuster 208 to cause the interface 195 to display a zoomed-in or enlarged view of reference path 176, as illustrated in FIG. 13.

Figure 13:
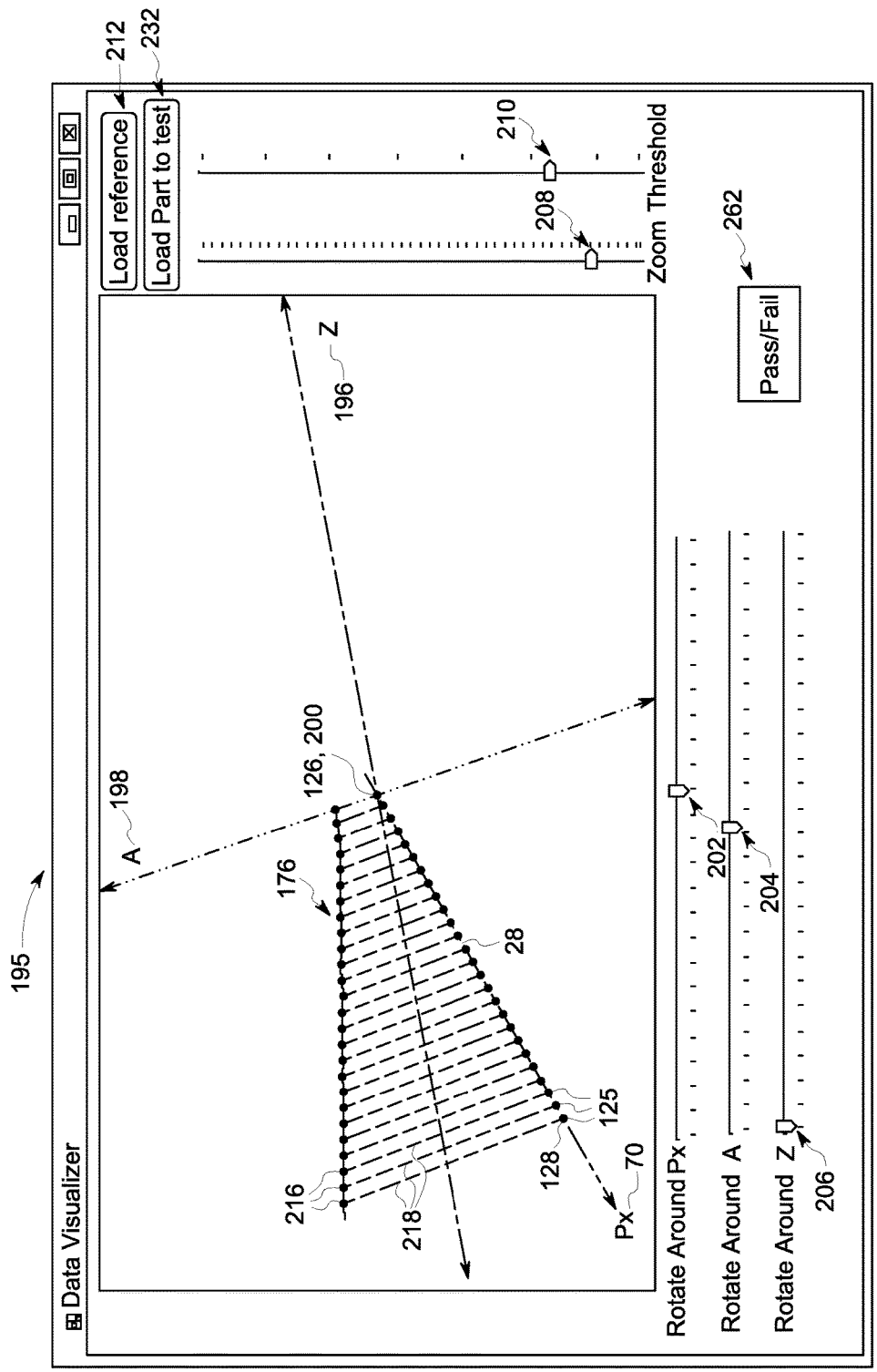
FIG. 13 is a top view of an embodiment of the graphical interface of the inspection system illustrating an example of the reference path after being rotated and enlarged.

As shown in FIG. 13, reference path 176 can extend relative to the probe travel axis Px 70. As shown in this example, the probe travel axis Px 70 has twenty-six, equally spaced-apart position points 125. Likewise, the reference path 176 has twenty-six, equally spaced-apart reference position points 216. Each position point 125 corresponds to an oppositely-located reference position point 216 as indicated through dotted correlation lines 218 shown for illustration purposes. The processor 12, under direction of the correlation module 19 (FIG. 1), matches or pairs the reference position points 216 on the reference path 176 with the position points 125 on the probe travel axis Px 70. The view or image shown in FIG. 13 provides an intuitive, graphical representation of the variations in the impedance plane based on the physical travel of the probe 108 relative to the tubular object 110 (FIG. 6).

Figure 14:
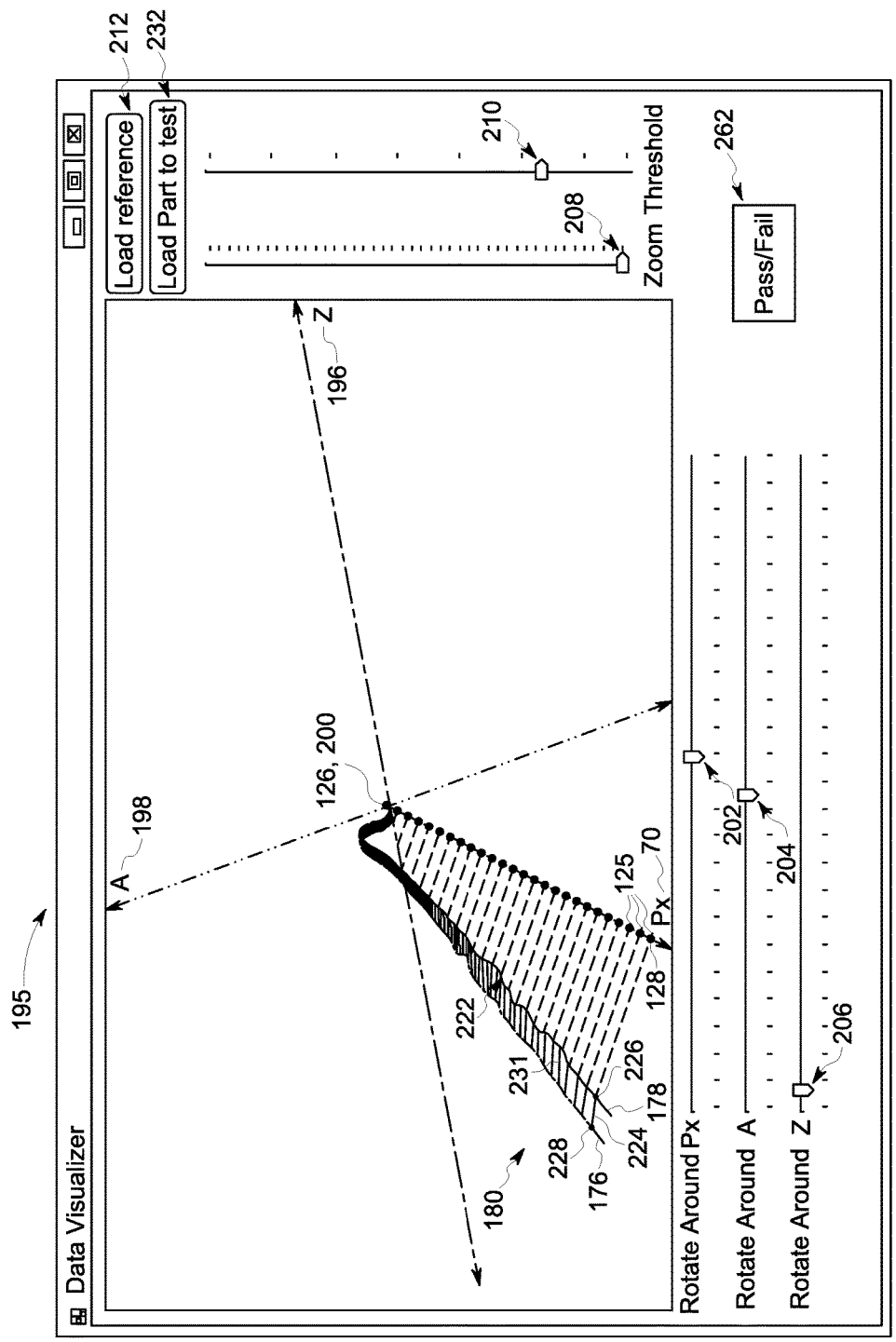
FIG. 14 is a top view of an embodiment of the graphical interface of the inspection system illustrating an example of the reference track having a plurality of rungs representing signal noise.

Referring to FIG. 14, to assess the effect of the presence of signal noise, the user, in an example, can press the load reference input element 212 again to represent the data associated with a second pass of the eddy current probe 108. In response, the interface 195 can display the reference path 178. As indicated by block 220 in FIG. 10, the interface 195 displays a noise reference track 180 defined or constructed by reference paths 176 and 178. As shown, the noise reference track 180 has a ladder-like structure including a plurality of noise rungs 222. Each noise rung 222 extends from one of the position points of reference path 178 to the oppositely-located or matched position point of reference path 176. For example, rung 224 connects, matches or otherwise relates position point 226 to position point 228. The variable width of the noise reference track 180 or the variable distance between the reference paths 176 and 178 represents the degree or extent of signal noise in the probing process. At this stage, as indicated by block 230 (FIG. 10), the user or system 10 records or notes the length, value or magnitude of the longest or greatest noise rung 231. This represents the greatest amount of signal noise present.

Figure 15:
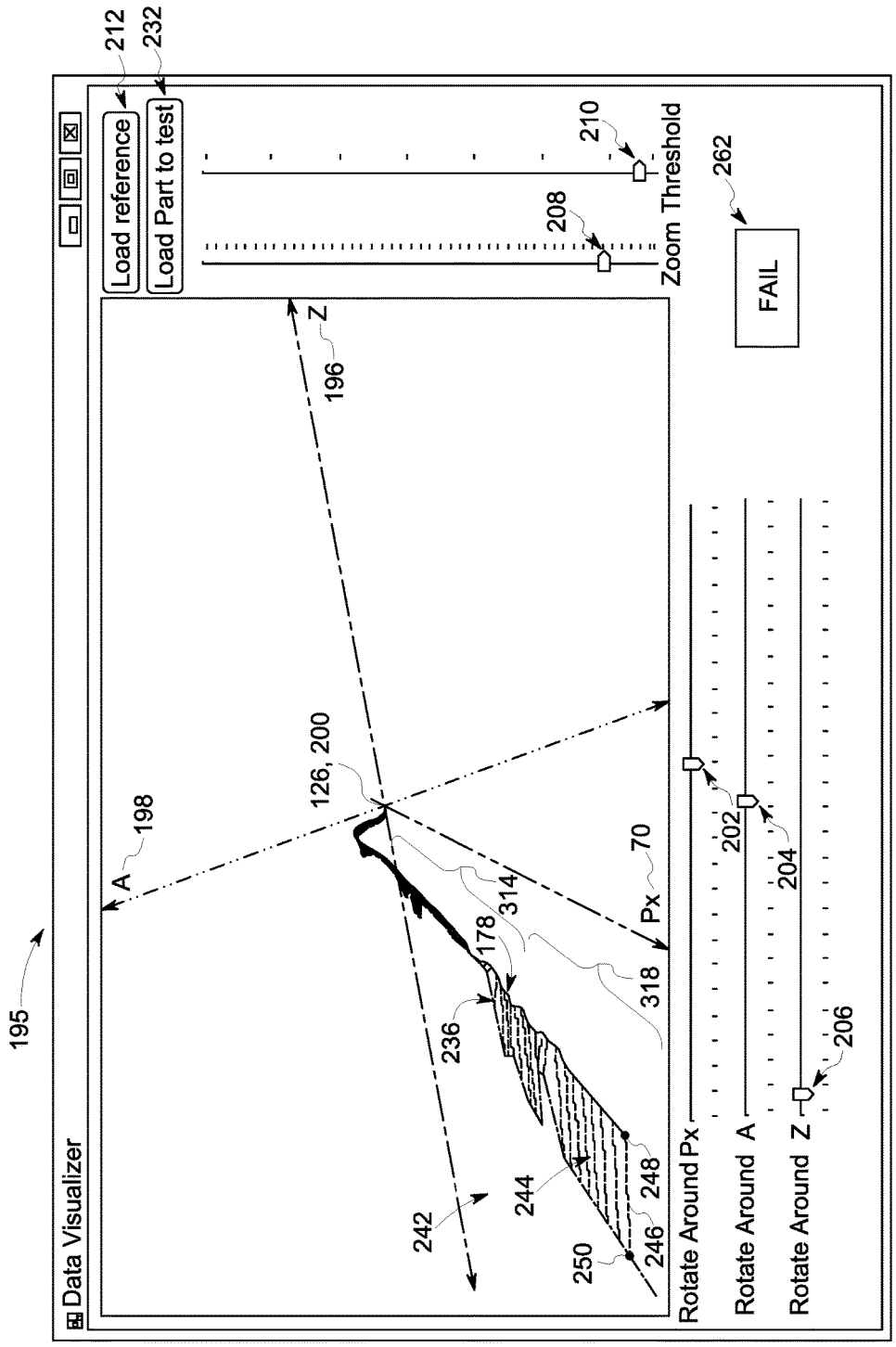
FIG. 15 is a top view of an embodiment of the graphical interface of the inspection system illustrating an example of the inspection track having a plurality of rungs representing deviations from a reference path, some of which represent flaws because they deviate more than a designated, maximum deviation setting.

Referring to FIG. 15, the user can then activate the load part input element 232. In response, the interface 195 hides or removes reference path 176, as indicated by block 234 in FIG. 10, while reference path 178 remains. Then, the interface 195 overlays or displays inspection path 236 (FIG. 15) as indicated by block 238 in FIG. 10. As indicated by block 240 in FIG. 10, the interface 195 displays an inspection track 242 (FIG. 15) defined or constructed by reference path 178 and inspection path 236. As shown, the inspection track 242 has a ladder-like structure including a plurality of inspection rungs 244. Each inspection rung 244 extends from one of the position points of reference path 178 to the oppositely-located or matched position point of inspection path 236. For example, rung 246 connects, matches or otherwise relates position point 248 to position point 250. As described further below, the variable width of the inspection track 242 or the variable distance between the reference path 178 and inspection path 236 represents the degree or extent of flaws or defects (if any) in the tubular object 110 (FIG. 6) inspected by the user.

As indicated by block 252 in FIG. 10, the user can then adjust one or more of the adjusters 202, 204, 206 and 208 (FIG. 15) to obtain a desired view of the inspection track 242 (FIG. 15). The user may then, as indicated by blocks 254 and 256 in FIG. 10, activate the threshold adjuster 210 (FIG. 15) to determine and set the desired threshold, maximum deviation value or maximum deviation setting 42 (FIG. 1). Knowing the extent or value of the signal noise, based on the greatest noise rung 231 (FIG. 14), the user can set the maximum deviation setting 42 to a value that is greater than the value associated with the greatest noise rung 231. Doing so can prevent the signal noise from creating a false failure or false indication of a flaw.

Next, as indicated by decision diamond 258 in FIG. 10, it can be determined whether one or more inspection rungs 244 of the inspection track 242 (FIG. 15) exceed the maximum deviation setting 42, a setting corresponding to the length of the greatest noise rung 231 (FIG. 14). This enables the user to visually determine whether, and at which locations, the inspection path 236 separates from the reference path 178 more than the length of the greatest noise rung 231. Any such separation can indicate a flaw or failure in the tubular object 110 (FIG. 6) according to failure conditions or criteria managed by the system 10.

In an embodiment, the maximum deviation setting 42 (FIG. 1) can be considered a single, continuous threshold setting having a shape that varies with, and conforms to, the physical profile of the tubular object 110. In other embodiments described below, the system 10 can apply a plurality of different maximum deviation settings 42 for different regions 114, 116 and 118 (FIG. 6) of the tubular object 110, where each such setting can be a continuous threshold setting having a shape that varies with, and conforms to, the profile of a particular region of the tubular object 110.

In one such embodiment, the evaluation setting data 40 can include a plurality of different thresholds or different maximum deviation settings 42 (FIG. 1). Referring to FIGS. 6 and 15, the system 10 enables the user to set, for example, a relatively low maximum deviation setting for region 114 of tubular object 110 and corresponding section 314 of the inspection track 242. The system 10 also enables the user to set a relatively high maximum deviation setting for region 118 of tubular object 110 and corresponding section 318 of the inspection track 242. In this way, the system 10 enables the user to apply different degrees or levels of quality scrutiny to different regions 114, 116 and 118 of the tubular object 110. Since different regions 114, 116 and 118 of the tubular object 110 can have, or can encounter, more signal noise than others, this also enables the user to apply greater maximum deviation settings for the regions with more signal noise. In this embodiment, the interface 195 can display a plurality of different maximum deviation outputs, not shown, indicating the different maximum deviations set by the user.

Depending upon the embodiment, the decision indicated in diamond 258 (FIG. 10) can be controlled by the user through human decision-making or by the processor 12 based on the logic module 16 (FIG. 1). As indicated by block 260, if the maximum deviation setting 42 is not exceeded, the interface 195 displays a pass alert, such as a green pass message, to indicate an inspection pass outcome at the outcome indicator 262 illustrated in FIG. 15. As indicated by block 264 in FIG. 10, if the maximum deviation setting 42 is exceeded, the interface 195 displays a failure alert, such as a red fail message, to indicate an inspection failure outcome at the outcome indicator 262 as illustrated in FIG. 14. Depending upon the embodiment and the user's strategy, any such failure outcome and failure alert can be based on a finding of a single inspection rung 244 (FIG. 15) that exceeds the maximum deviation setting 42 or on a plurality of inspection rungs 244 that exceed the maximum deviation setting 42. At this stage, the evaluation mode ends as indicated by block 266.

In the example shown in FIG. 15, the user selected the value of the greatest noise rung 231, shown in FIG. 14, as the maximum deviation setting 42. Therefore, the system 10 indicated no failure outcome for track section 314 of the inspection track 242. However, several of the inspection rungs 244 of track section 318 are greater than the noise rung 231 (FIG. 14). Therefore, the system 10 indicated a failure outcome for track section 318. The interface 195 indicated the failure outcome by displaying the "FAIL" message at outcome indicator 262 as illustrated in FIG. 15. In an embodiment, the interface 195 emphasizes the failure outcomes by graphically generating the failure-causing rungs 244 in red or through other graphical emphasis methods.

In an embodiment, the logic module 16 can include a maximum deviation setting generator to facilitate the determination of suitable maximum deviation settings 42. Such maximum deviation setting generator can be coupled to the average reference data 20 (FIG. 1). Applying suitable statistical formulas, the maximum deviation setting generator can automatically determine optimal or recommended maximum deviation settings for the evaluation mode. This can reduce the risk of human error and increase efficiency in the inspection process. In an example, the maximum deviation setting generator, at each position point 125 (FIG. 6), can determine the object-to-object variation data by comparing multiple pairs of reference objects 22. Then, the maximum deviation setting generator can record and automatically set the maximum deviation setting based on an average or suitable multiple of such variation data.

As described above, the interface 195 shown in FIGS. 11-15 includes a plurality of different control elements operable by the user to provide inputs and control commands to the processor 12. In an embodiment, the interface 195 can include one or more part specification input elements. The one or more part specification input elements can enable the user to define and control the start boundary for the tubular object 110 (FIG. 6) and the end boundary for the tubular object 110. If the eddy current probe 108 (FIG. 6) travels in open air for a period before reaching the tubular object 110, the logic module 16 can direct the processor 12 to inhibit or suspend the probe signal generation until the eddy current probe 108 reaches such user-specified start boundary. Likewise, when the eddy current probe 108 reaches the end boundary, the processor 12 can inhibit or stop signals from being generated by the eddy current probe 108. In this way, the interface 195 can exclude or reduce distracting air-based signals from the inspection track 242 (FIG. 15).

Figure 16:
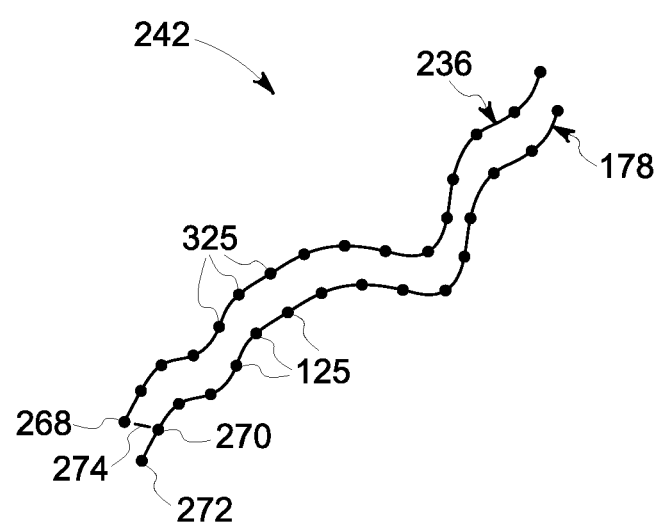
FIG. 16 is a top view of an embodiment of an example of the inspection track of the inspection system illustrating non-matched or misaligned position points which have been associated through the interpolation module.

Referring to FIG. 16, it is possible that the position points 125 on the reference path 178 might be offset from, and not directly across from, the corresponding position points 325 on the inspection path 236. There can therefore be one or more non-matched or misaligned position points on inspection track 242. In such event, the interpolation module 33 can direct the processor 12, on a point-by-point basis, to determine the position point on reference path 178 that is closest to the position point on the inspection path 236. For example, the processor 12 can determine that the position point 268 is closer to position point 270 than position point 272. Based on that determination, the processor 12 can associate point 268 with point 270 and also display an inspection rung 274 between the points 268 and 270.

Referring back to FIG. 1, in an embodiment, the system 10 can be stored in a database or server, and the processor 12 can access such sever over any suitable type of network. Depending upon the embodiment, the network can include one or more of the following: a wired network, a wireless network, a local area network (LAN), an extranet, an intranet, a wide area network (WAN) (including, but not limited to, the Internet), a virtual private network (VPN), an interconnected data path across which multiple devices may communicate, a peer-to-peer network, a telephone network, portions of a telecommunications network for sending data through a variety of different communication protocols, a Bluetooth communication network, a radio frequency (RF) data communication network, an infrared (IR) data communication network, a satellite communication network or a cellular communication network for sending and receiving data through short messaging service (SMS), multimedia messaging service (MMS), hypertext transfer protocol (HTTP), direct data connection, Wireless Application Protocol (WAP), email or any other suitable message transfer service or format.

As shown in FIG. 1, in an embodiment, the processor 12 or logic module 16 can include a data processor or a central processing unit (CPU). The system 10 can include one or more data storage devices, including, but not limited to, a hard drive with a spinning magnetic disk, a Solid-State Drive (SSD), a floppy disk, an optical disk (including, but not limited to, a CD or DVD), a Random Access Memory (RAM) device, a Read-Only Memory (ROM) device (including, but not limited to, programmable read-only memory (PROM), electrically erasable programmable read-only memory (EPROM), electrically erasable programmable read-only memory (EEPROM)), a magnetic card, an optical card, a flash memory device (including, but not limited to, a USB key with non-volatile memory, any type of media suitable for storing electronic instructions or any other suitable type of computer-readable storage medium.

The I/O devices 14 can include any device operable to communicate with the processor 12 or system 10, including, but not limited to, a personal computer (PC) (including, but not limited to, a desktop PC, a laptop or a tablet), smart television, Internet-enabled TV, person digital assistant, smartphone, cellular phone or mobile communication device. In one embodiment, I/O device 14 has at least one input device (including, but not limited to, a touchscreen, a keyboard, a microphone, a sound sensor or a speech recognition device) and at least one output device (including, but not limited to, a speaker, a display screen, a monitor or an LCD).

In an embodiment, the computer-readable instructions, algorithms and logic of the system 10 (including the logic module 16) are implemented with any suitable programming or scripting language, including, but not limited to, C, C++, Java, COBOL, assembler, PERL, Visual Basic, SQL Stored Procedures or Extensible Markup Language (XML). The system 10 can be implemented with any suitable combination of data structures, objects, processes, routines or other programming elements.

In an embodiment, the interface 195 of the system 10 can be a Graphical User Interface (GUI) structured based on a suitable programming language. The GUI can include, in an embodiment, multiple windows, pull-down menus, buttons, scroll bars, iconic images, wizards, the mouse symbol or pointer, and other suitable graphical elements. In one embodiment, the GUI incorporates multimedia, including, but not limited to, sound, voice, motion video and virtual reality interfaces to generate outputs of the system 10.

In an embodiment, the memory devices and data storage devices described above can be non-transitory mediums that store or participate in providing instructions to a processor for execution. Such non-transitory mediums can take different forms, including, but not limited to, non-volatile media and volatile media. Non-volatile media can include, for example, optical or magnetic disks, flash drives, and any of the storage devices in any computer. Volatile media can include dynamic memory, such as main memory of a computer. Forms of non-transitory computer-readable media therefore include, for example, a floppy disk, flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, or any other medium from which a computer can read programming code and/or data. Many of these forms of computer readable media may be involved in carrying one or more sequences of one or more instructions to a processor for execution. In contrast with non-transitory mediums, transitory physical transmission media can include coaxial cables, copper wire and fiber optics, including the wires that comprise a bus within a computer system, a carrier wave transporting data or instructions, and cables or links transporting such a carrier wave. Carrier-wave transmission media can take the form of electric or electromagnetic signals, or acoustic or light waves such as those generated during RF and IR data communications.

As will be appreciated by one skilled in the art, aspects of the disclosed subject matter may be embodied as a system, method, or computer program product. Accordingly, aspects of the disclosed subject matter may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the disclosed subject matter may take the form of a computer program product embodied in one or more computer readable medium(s) having computer readable program code embodied thereon.

Aspects of the disclosed subject matter are described herein referring to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In an embodiment illustrated in FIG. 1, the system 10 provides a plurality of advantageous, technical effects. The logic module 16 tracks positional information (e.g., position count) with each incremental movement of the probe 48 relative to the object 18. When the probe 48 reaches each position point, the system 10 performs the following functions: (a) recording of the position count corresponding to such position point; and (b) recording of the probe's one or more signal values corresponding to the characteristic of the object 18 at such position point. The system 10 synchronizes or correlates such position count with such signal values. Using this information, a combination of probe positional data and probe signal value data, the system 10 displays a spatially-intuitive inspection path. The intuitive inspection path varies with the variation in the signal values at the different position points to facilitate the inspection and evaluation of objects.

Additional embodiments can include any one of the embodiments described above, where one or more of its components, functionalities or structures can be interchanged with, replaced by or augmented by one or more of the components, functionalities or structures of a different embodiment described above.

It should be understood that various changes and modifications to the embodiments described herein will be apparent to those skilled in the art. Such changes and modifications can be made without departing from the spirit and scope of the present disclosure and without diminishing its intended advantages. It is therefore intended that such changes and modifications be covered by the appended claims.

Although several embodiments of the disclosure have been disclosed in the foregoing specification, it is understood by those skilled in the art that many modifications and other embodiments of the disclosure will come to mind to which the disclosure pertains, having the benefit of the teaching presented in the foregoing description and associated drawings. It is thus understood that the disclosure is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the present disclosure, nor the claims which follow.

To the extent that the claims recite the phrase "at least one of" in reference to a plurality of elements, this is intended to mean at least one or more of the listed elements, and is not limited to at least one of each element. For example, "at least one of an element A, element B, and element C," is intended to indicate element A alone, or element B alone, or element C alone, or any combination thereof. "At least one of element A, element B, and element C" is not intended to be limited to at least one of an element A, at least one of an element B, and at least one of an element C.

This written description uses examples to disclose the disclosed subject matter, including the best mode, and also to enable any person skilled in the art to practice the disclosed subject matter, including making and using any devices or systems and performing any incorporated methods. The patentable scope of the disclosed subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An inspection system comprising:
   at least one data processor configured to operate with a probe, a display device, and a position tracker to inspect an object; and
   a data storage device storing executable instructions, the data storage device being accessible by the at least one processor, wherein, when executed by the at least one processor, the executable instructions implement operations comprising:
   displaying at least one probe travel axis on the display device, the at least one probe travel axis extending through a plurality of inspection position points,
   generate a first inspection value based on a first signal from the probe, the first inspection value characterizing a characteristic of the object at a first object point,
   generate a second inspection value based on a second signal from the probe, the second inspection value characterizing the characteristic of the object at a second object point,
   displaying an inspection path based on the first inspection position and the second inspection position, the inspection path extending relative to the at least one probe travel axis, and
   displaying a reference path extending relative to the at least one probe travel axis, wherein the inspection path and the reference path form a track characterizing information related to the characteristic of the object at the first and second object points.

2. The inspection system of claim 1, wherein, the first and second inspection values are each selected from a group consisting of an impedance value, a phase angle value, and an eddy current factor value.

3. The inspection system of claim 1, wherein the first and second inspection values are each selected from a group consisting of a signal strength value, a time value, and an ultrasound factor value.

4. The inspection system of claim 1, wherein the characteristic is selected from a group consisting of a physical characteristic, an electrical characteristic, and a chemical characteristic.

5. The inspection system of claim 1, wherein
the first signal is based on a first dimension of the object; and
the second signal is based on a second dimension of the object, wherein the first and second dimensions are different.

6. The inspection system of claim 1, wherein the at least one processor is operable according to the instructions to operate with the display device to display at least one inspection axis intersecting with the at least one probe travel axis.

7. The inspection system of claim 1, wherein:
the at least one processor is operable according to the instructions to receive a maximum deviation setting relating to a maximum deviation between a first reference value of the reference path and the first inspection value of the inspection path; and
the at least one processor is operable according to the instructions to operate with the display device to generate a failure outcome output if a difference between the first reference value of the reference path and the first inspection value of the inspection path, is greater than the maximum deviation.

8. The inspection system of claim 7, wherein the at least one processor is operable according to the instructions to operate with the display device to generate a pass outcome output if any difference between the first reference value of the reference path and the first inspection value of the inspection path, is equal to or less than the maximum deviation.

9. An inspection system comprising:
at least one processor configured to operate with a probe and a position tracker to inspect an object, the at least one processor being programmed to operate with a display device to
display at least one probe travel axis, the at least one probe travel axis extending through a plurality of inspection position points;
generate a first inspection value based on a first signal from the probe, the first inspection value characterizing a characteristic of the object at a first object point;
generate a second inspection value based on a second signal from the probe, the second inspection value characterizing a characteristic of the object at a second object point;
perform an association, the association including
associating the first inspection value with the first position point, and
associating the second inspection value with the second position point;
display an inspection path based on the association, the inspection path extending relative to the at least one probe travel axis; and
display a reference path extending relative to the at least one probe travel axis, the reference path being based on a first reference value corresponding to the characteristic at the first object point, and a second reference value corresponding to the characteristic at the second object point.

10. The inspection system of claim 9, wherein, the first and second inspection values are each selected from a group consisting of an impedance value, a phase angle value, and an eddy current factor value.

11. The inspection system of claim 10, wherein the first and second inspection values are each selected from a group consisting of a signal strength value, a time value, and an ultrasound factor value.

12. The inspection system of claim 9, wherein the characteristic is selected from a group consisting of a physical characteristic, an electrical characteristic, and a chemical characteristic.

13. The inspection system of claim 9, wherein:
the first inspection value is derived from a first signal received from the probe, the first signal being based on a first dimension of the object;
the second inspection value is derived from a second signal received from the probe, the second signal being based on a second dimension of the object, there being a difference between the first and second dimensions; and
the first and second signals are different based on the difference between the first and second dimensions of the object.

14. The inspection system of claim 9, wherein the at least one processor is programmed to operate with the display device to display at least one inspection axis intersecting with the at least one probe travel axis.

15. The inspection system of claim 9, wherein the at least one processor is programmed to:
operate with the display device to receive a maximum deviation setting related to a distance between the inspection path and the reference path; and
generate an output depending upon the distance.

16. The inspection system of claim 15, wherein:
the at least one processor is operable according to the instructions to operate with the display device to generate a failure outcome output if the inspection path is further from the reference path than the distance; and
the at least one processor is operable according to the instructions to operate with the display device to generate a pass outcome output if the inspection path is not further from the reference path than the distance.

17. The inspection system of claim 9, further comprising
a position tracker coupled to the at least one processor, the position tracker being configured to be operated in the reference mode and the inspection mode;
a memory device coupled to the at least one processor, the memory device storing a plurality of instructions;
a display device coupled to the at least one processor; and
a probe coupled to the at least one processor, the probe being configured to be operated in a reference mode and an inspection mode, wherein the probe is operable to
transmit a plurality of outgoing reference signals toward a reference object extending along a reference object axis when in the reference mode,
receive a plurality of incoming reference signals resulting from interaction of the outgoing reference signals with the reference object when in the reference mode, transmit a plurality of outgoing inspection signals toward the object extending along an object axis when in the inspection mode, and receive a plurality of incoming inspection signals resulting from interaction of the outgoing inspection signals with the object when in the inspection mode.

18. An inspection method, comprising:

graphically displaying at least one probe travel axis, the at least one probe travel axis extending through a plurality of inspection position points;

generating a first inspection value based on a first signal from the probe, the first inspection value characterizing a characteristic of the object at a first object point;

generating a second inspection value based on a second signal from the probe, the second inspection value characterizing the characteristic of the object at a second object point;

performing an association that includes associating the first inspection value with the first position point, and associating the second inspection value with the second position point;

displaying an inspection path based on the association, the inspection path extending relative to the at least one probe travel axis; and displaying a reference path extending relative to the at least one probe travel axis, the reference path being derived from an inspection of a reference characteristic of a reference object, wherein the inspection path and the reference path form a track that characterizes a difference between the characteristic of the object and the reference characteristic of the reference object.

19. The inspection method of claim 18, wherein the reference path is based on a first reference value corresponding the reference characteristic at the first object point, and a second reference value corresponding the reference characteristic at the second object point;

the first and second inspection values are each selected from a first group consisting of an impedance value, a phase angle value, an eddy current factor value, a signal strength value, a time value, and an ultrasound factor value; and the characteristic is selected from a second group consisting of a physical characteristic, an electrical characteristic, and a chemical characteristic.

20. The inspection method of claim 19, comprising:

receiving an input of a maximum deviation relating to a distance between the inspection path and the reference path; and generating a failure outcome output as a result of the distance being greater than the maximum deviation.

* * * * *